US010308984B2

(12) United States Patent
Thornton et al.

(10) Patent No.: US 10,308,984 B2
(45) Date of Patent: Jun. 4, 2019

(54) INTERNAL CONTROL NUCLEIC ACIDS FOR AMPLIFICATION

(71) Applicant: Becton, Dickinson and Company, Franklin Lakes, NJ (US)

(72) Inventors: Keith Edward Thornton, Owings Mills, MD (US); Danielle Koffenberger, Bartlett, NH (US); Paul Madepogu, Baltimore, MD (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days.

(21) Appl. No.: 15/730,434

(22) Filed: Oct. 11, 2017

(65) Prior Publication Data

US 2018/0112262 A1    Apr. 26, 2018

Related U.S. Application Data

(62) Division of application No. 14/388,704, filed as application No. PCT/US2013/031032 on Mar. 13, 2013, now Pat. No. 9,822,402.

(60) Provisional application No. 61/617,562, filed on Mar. 29, 2012.

(51) Int. Cl.
*C12Q 1/6853* (2018.01)
*C12Q 1/6876* (2018.01)

(52) U.S. Cl.
CPC ......... *C12Q 1/6853* (2013.01); *C12Q 1/6876* (2013.01); *C12Q 2600/166* (2013.01)

(58) Field of Classification Search
None
See application file for complete search history.

(56) References Cited

U.S. PATENT DOCUMENTS

| | | | | |
|---|---|---|---|---|
| 6,680,370 | B1 * | 1/2004 | Miyata | C07K 14/47 530/350 |
| 6,783,934 | B1 | 8/2004 | McMillan et al. | |
| 6,794,133 | B1 | 9/2004 | Ausubel et al. | |
| 6,977,148 | B2 | 12/2005 | Dean et al. | |
| 8,034,588 | B2 | 10/2011 | Bergeron et al. | |
| 9,822,402 | B2 * | 11/2017 | Thornton | C12Q 1/6876 |
| 2004/0005561 | A1 * | 1/2004 | Gaiger | C07K 14/47 435/6.16 |
| 2009/0208948 | A1 * | 8/2009 | Paquette | C07H 21/00 435/6.15 |
| 2010/0267012 | A1 | 10/2010 | Bergeron et al. | |

FOREIGN PATENT DOCUMENTS

| | | |
|---|---|---|
| JP | 2011-155855 A | 8/2011 |
| WO | WO 2001/71042 A2 | 9/2001 |
| WO | WO 2004/104229 A2 | 12/2004 |
| WO | WO 2005/047462 A2 | 5/2005 |

OTHER PUBLICATIONS

GenBank Accession No. AB022762 for *Drosophila melanogaster* retrotransposon aurora DNA (Dec. 20, 2010 [online], [retrieved on May 8, 2018], retrieved from the Internet: <URL: https://www.ncbi.nlm.nih.gov/nuccore/AB022762.1?report=genbank&log$= seqview>. (Year: 2010).*
Venken et al. Nature Methods 2009; 6: 431-434. (Year: 2009).*
Kanamori et al. Genes & Genetic Systems 1998; 73: 385-396. (Year: 1998).*
GenBank Accession No. AC246436 for *Drosophila melanogaster* clone BACR24N15, complete sequence. Dec. 21, 2011 [online ], [retrieved on Sep. 5, 2018], retrieved from the Internet: <URL: https://www.ncbi.nlm.nih.gov/nuccore/ac246436>. (Year: 2011).*
Adams, M., et al., "The Genome Sequence of *Drosophilia melanogaster*", Science, DOI: 10.1126/science.287 .5461 .2185, vol. 287, Mar. 24, 2000, pp. 2185-2195.
Benson, DA, et al., "GenBank", Nucleic Acids Research, DOI: 10.1093/nar/gki063, vol. 33, D34-D-38, Oct. 5, 2004. http://ncbi.nlm.nih.gov.
International Search Report and Written Opinion in PCT/US13/31032, dated Aug. 15, 2013.
Marras, S., "Selection of Fluorophore and Quencher Pairs for Fluoroscent Nucleic Acid Hybridization Probes", molecular-beacons.org/download/marras,mmb06%28335%293.pdf.
Extended European Search Report dated Feb. 26, 2016 in Application No. 13769167.1.
Database EMBL [Online] Jan. 16, 2009 (Jan. 16, 2009), "CH322-41D21.y CHORI-322 *Drosophilia melanogaster* genomic clone CH322-41D21, genomic survey sequence.", XP002753330, retrieved from EBI accession No. EM_GSS:FI463486 Database accession No. FI463486.
Office Action dated Sep. 7, 2016 in Chinese Application No. 201380026175.3 with English Translation.
Office Action dated Jul. 28, 2017 in European Application No. 13769167.1.
Venken et al., "Versatile P[acman] BAC libraries for transgenesis studies in *Drosophila melanogaster*", Nature Methods, vol. 6, No. 6, pp. 431-436, Jun. 2009.
Office Action dated Mar. 10, 2017 in U.S. Appl. No. 14/388,704.
Extended European search report dated Feb. 12, 2019 in Application No. 18193712.9.

* cited by examiner

*Primary Examiner* — Angela M. Bertagna
(74) *Attorney, Agent, or Firm* — Knobbe, Martens, Olson & Bear, LLP

(57) ABSTRACT

Nucleic acids sequences that can be used for nucleic acid amplification, for example quantitative nucleic acid amplification, are provided herein.

20 Claims, 6 Drawing Sheets

Specification includes a Sequence Listing.

Figure 2A

```
5'  tcgttgggaaccggagctgaatgaagccataccaaacgacgagcgtgacaccacgatgcctgtagcaatggcaacaacgttgcgcaaactattaactggc
    +---+---+---+---+---+---+---+---+---+---+---+---+---+---+---+---+---+---+---+---+  100

5'  gaactacttactctagcttcccggcaacaattaatagactggatggaggcggataaagttgcaggaccacttctgcgctcggcccttccggctggctggt
    +---+---+---+---+---+---+---+---+---+---+---+---+---+---+---+---+---+---+---+---+  200

5'  ttattgctgataaatctggagccggtgagcgtggttctcgcggtatcattgcagcactggggccagatggtaagccctcccgtatcgtagttatctacac
    +---+---+---+---+---+---+---+---+---+---+---+---+---+---+---+---+---+---+---+---+  300

5'  gacggggagtcaggcaactatggatgaacgaaatagacagatcgctgagataggtgcctcactgattaagcattggtaactgtcagaccaagtttactca
    +---+---+---+---+---+---+---+---+---+---+---+---+---+---+---+---+---+---+---+---+  400

5'  tatatactttagattgatttaaaacttcattttaatttaaaaggatctaggtgaagatccttttgataatctcatgaccaaaatcccttaacgtgagt
    +---+---+---+---+---+---+---+---+---+---+---+---+---+---+---+---+---+---+---+---+  500

5'  tttcgttccactgagcgtcagaccccgtagaaaagatcaaaggatcttcttgagatcctttttttctgcgcgtaatctgctgcttgcaaacaaaaaaacc
    +---+---+---+---+---+---+---+---+---+---+---+---+---+---+---+---+---+---+---+---+  600

5'  accgctaccagcggtggtttgtttgccggatcaagagctaccaactctttttccgaaggtaactggcttcagcagagcgcagataccaaatactgttctt
    +---+---+---+---+---+---+---+---+---+---+---+---+---+---+---+---+---+---+---+---+  700

5'  ctagtgtagccgtagttaggccaccacttcaagaactctgtagcaccgcctacatacctcgctctgctaatcctgttaccagtggctgctgccagtggcg
    +---+---+---+---+---+---+---+---+---+---+---+---+---+---+---+---+---+---+---+---+  800

5'  ataagtcgtgtcttaccgggttggactcaagacgatagttaccggataaggcgcagcggtcgggctgaacgggggttcgtgcacacagcccagcttgga
    +---+---+---+---+---+---+---+---+---+---+---+---+---+---+---+---+---+---+---+---+  900

5'  gcgaacgacctacaccgaactgagatacctacagcgtgagctatgagaaagcgccacgcttcccgaagggagaaaggcggacaggtatccggtaagcggc
    +---+---+---+---+---+---+---+---+---+---+---+---+---+---+---+---+---+---+---+---+  1000

5'  agggtcggaacaggagagcgcacgagggagcttccaggggaaacgcctggtatctttatagtcctgtcgggtttcgccacctctgacttgagcgtcgat
    +---+---+---+---+---+---+---+---+---+---+---+---+---+---+---+---+---+---+---+---+  1100

5'  ttttgtgatgctcgtcagggggcggagcctatggaaaaacgccagcaacgcggccttttacggttcctggccttttgctggccttttgctcacatgtt
    +---+---+---+---+---+---+---+---+---+---+---+---+---+---+---+---+---+---+---+---+  1200

5'  ctttcctgcgttatcccctgattctgtggataaccgtattaccgcctttgagtgagctgataccgctcgccgcagccgaacgaccgagcgcagcgagtca
    +---+---+---+---+---+---+---+---+---+---+---+---+---+---+---+---+---+---+---+---+  1300

5'  gtgagcgaggaagcggaagagcgcccaatacgcaaaccgcctctccccgcgcgttggccgattcattaatgcagctggcacgacaggtttcccgactgga
    +---+---+---+---+---+---+---+---+---+---+---+---+---+---+---+---+---+---+---+---+  1400

5'  aagcgggcagtgagcgcaacgcaattaatgtgagttagctcactcattaggcaccccaggctttacactttatgcttccggctcgtatgttgtgtggaat
    +---+---+---+---+---+---+---+---+---+---+---+---+---+---+---+---+---+---+---+---+  1500

5'  tgtgagcggataacaatttcacacaggaaacagctatgaccatgattacgccaagcttggatcctatctcctttcGATGCTCCCTTCGGCATCCATTAAC
    +---+---+---+---+---+---+---+---+---+---+---+---+---+---+---+---+---+---+---+---+  1600
                                                                                    Drosophila Scaffold Sequence (200bp)

5'  CTGGCACTCACCTTGCGTATAGCAGGATCTAGCCGTGTGCCCGCTTCGCAGGCAATTGAAGCAGAGCtGATGCCTCTTCACATTGCTCCACCTTTCCTGT
    +---+---+---+---+---+---+---+---+---+---+---+---+---+---+---+---+---+---+---+---+  1700
                    [DrosFP5 (SEQ ID NO: 3) >              [Drosprobe Sign-T1-ROX-B2 -SEQ ID NO: 2]
    ─────────────────────────── Drosophila Scaffold Sequence (200bp) ───────────────────◆─

5'  GGCGAAGCTCCAATAAATTTTCTGCAGTTCAATATTTCATGCTGTCCTCCACAAATGGGACAACCTCCATGCCGAgaaagttgagaccatggaattcact
    +---+---+---+---+---+---+---+---+---+---+---+---+---+---+---+---+---+---+---+---+  1800
                                            < DrosRP5 (SEQ ID NO: 4)]
    ─────────────────── Drosophila Scaffold Sequence (200bp) ───────────────────
```

Figure 2B

```
ggccgtcgttttacaacgtcgtgactgggaaaaccctggcgttacccaacttaatcgccttgcagcacatccccctttcgccagctggcgtaatagcgaa                1900
gaggcccgcaccgatcgcccttcccaacagttgcgcagcctgaatggcgaatggcgcctgatgcggtattttctccttacgcatctgtgcggtatttcac                2000
accgcatacgtcaaagcaaccatagtacgcgccctgtagcggcgcattaagcgcggcgggtgtggtggttacgcgcagcgtgaccgctacacttgccagc                2100
gccctagcgcccgctcctttcgctttcttcccttcctttctcgccacgttcgccggctttccccgtcaagctctaaatcggggctccctttagggttcc                2200
gatttagtgctttacggcacctcgaccccaaaaaacttgatttgggtgatggttcacgtagtgggccatcgccctgatagacggttttcgccctttgac                2300
gttggagtccacgttctttaatagtggactcttgttccaaactggaacaacactcaaccctatctcgggctattcttttgatttataagggattttgccg                2400
atttcggcctattggttaaaaaatgagctgatttaacaaaaatttaacgcgaattttaacaaaatattaacgtttacaattttatggtgcactctcagta                2500
caatctgctctgatgccgcatagttaagccagccccgacacccgcaacacccgctgacgcgcctgacgggcttgtctgctcccggcatccgcttacag                  2600
acaagctgtgaccgtcaacgggagctgcatgtgtcagaggttttcaccgtcatcaccgaaacgcgcgacccgaaagggcctcgtgatacgcctatttta                 2700
taggttaatgtcatgataataatggtttcttagacgtcaggtggcacttttcggggaaatgtgcgcggaacccctatttgtttatttttctaaatacatt                2800
caaatatgtatccgctcatgagacaataaccctgataaatgcttcaataatattgaaaaggaagagtatgagtattcaacatttccgtgtcgcccttat                 2900
tccctttttgcggcattttgccttcctgtttttgctcacccagaaacgctggtgaaagtaaaagatgctgaagatcagttgggtgcacgagtgggttac                 3000
atcgaactggatctcaacagcggtaagatccttgagagttttcgccccgaagaacgttttccaatgatgagcacttttaaagttctgctatgtggcgcgg                3100
tattatcccgtattgacgccgggcaagagcaactcggtcgccgcatacactattctcagaatgacttggttgagtactcaccagtcacagaaaagcatct                3200
tacggatggcatgacactaagagaattatgcagtgctgccataaccatgagtgataacactgcggccaacttacttctgacaacgatcggaggaccgaag                3300
gagctaaccgcttttttgcacaacatgggggatcatgtaactcgccttga    SEQ ID NO: 8
```

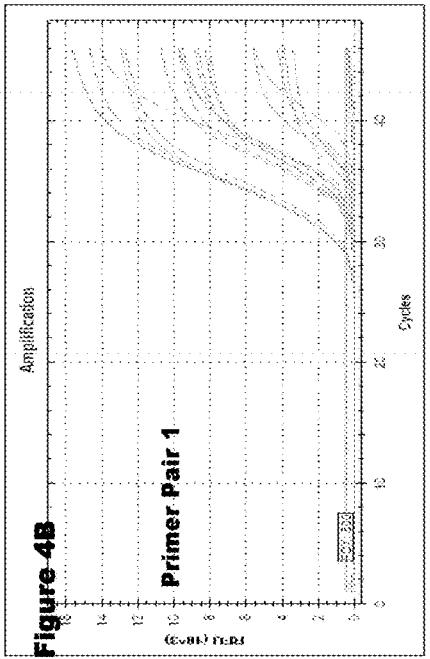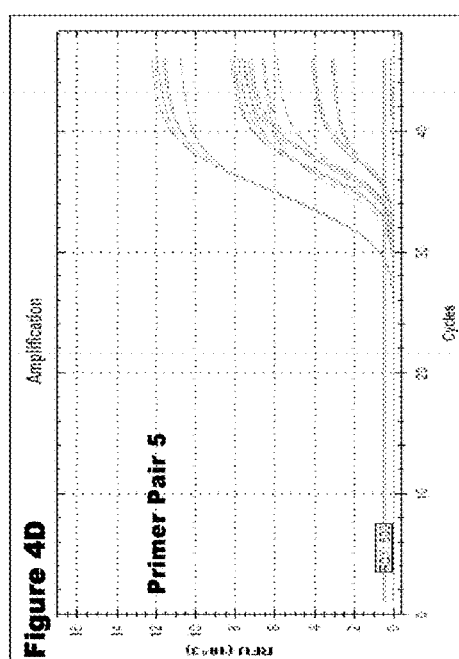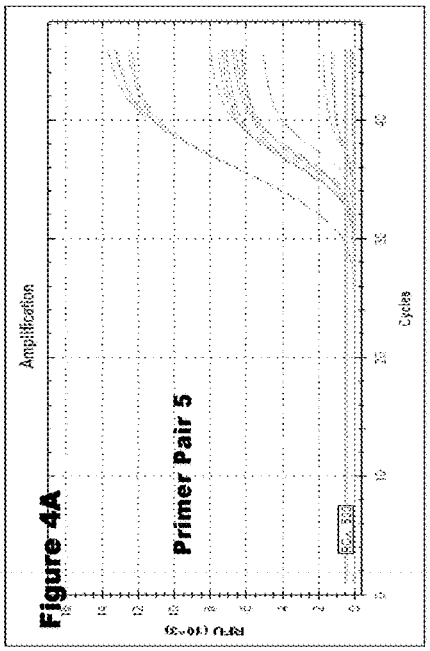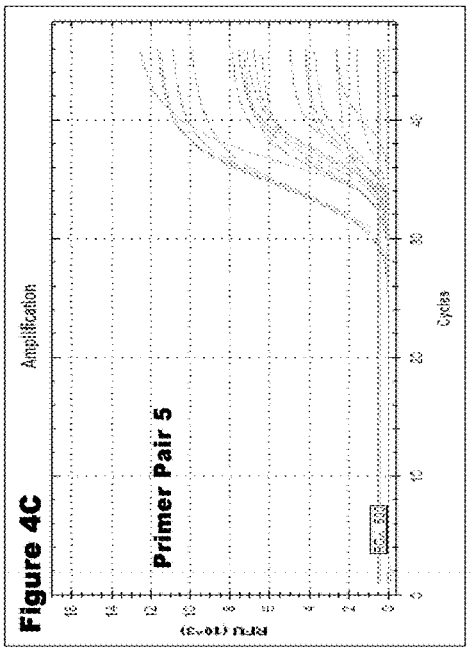

Figure 5

% Efficiency = 90.6%  Slope: -3.56  R2: 0.994
Threshold 500 - Stratagene Instrument

| Copies/rxn | DrosScaff1 Plasmid - Set 1.1 (Primer Pair 1) | | | | | | |
|---|---|---|---|---|---|---|---|
| | 5.0E+05 | 5.0E+04 | 5.0E+03 | 5.0E+02 | 5.0E+01 | 5.0E+00 | NTC |
| | 21.39 | 25.27 | 27.65 | 31.52 | 34.95 | U | U |
| | 21.39 | 24.17 | 27.81 | 32.18 | 35.26 | 39.47 | U |
| Inst 4 | 21.46 | 23.6 | 27.44 | 31.98 | 35.38 | 38.43 | U |
| | 21.05 | 23.97 | 28.2 | 31.23 | 35.45 | U | U |
| Ct Mean | 21.32 | 24.25 | 27.78 | 31.73 | 35.26 | 38.95 | |
| StDev | 0.18 | 0.72 | 0.32 | 0.43 | 0.22 | 0.74 | |
| CV | 0.87% | 2.96% | 1.16% | 1.36% | 0.63% | 1.89% | |

% Efficiency = 90.6%  Slope: -3.56  R2: 0.993
Threshold 500 - Stratagene Instrument

| Copies/rxn | DrosScaff1 Plasmid - Set 5 (Primer Pair 5) | | | | | | |
|---|---|---|---|---|---|---|---|
| | 5.0E+05 | 5.0E+04 | 5.0E+03 | 5.0E+02 | 5.0E+01 | 5.0E+00 | NTC |
| | 19.75 | 22.65 | 27.19 | 30.12 | 34.13 | U | U |
| | 19.6 | 22.62 | 26.11 | 29.72 | 34.54 | U | 37.00 |
| Inst 4 | 19.53 | 22.95 | 26.52 | 30.46 | 34.35 | U | U |
| | 19.72 | 22.69 | 26.69 | 29.86 | 33.99 | 36.07 | U |
| Ct Mean | 19.65 | 22.73 | 26.63 | 30.04 | 34.25 | 36.07 | |
| StDev | 0.10 | 0.15 | 0.45 | 0.33 | 0.24 | | |
| CV | 0.52% | 0.66% | 1.68% | 1.08% | 0.71% | | |

SEQUENCE LISTING

```
<160> NUMBER OF SEQ ID NOS: 16

<210> SEQ ID NO 1
<211> LENGTH: 200
<212> TYPE: DNA
<213> ORGANISM: Artificial Sequence
<220> FEATURE:
<223> OTHER INFORMATION: Synthetic DNA

<400> SEQUENCE: 1
gatgctccct tcggcatcca ttaacctggc actcaccttg cgtatagcag gatctagccg    60
```

```
tgtgcccgct tcgcaggcaa ttgaagcaga gctgatgcct cttcacattg ctccaccttt    120
cctgtggcga agctccaata aatttctgc agttcaatat ttcatgctgt cctccacaaa    180
tgggacaacc tccatgccga                                                200
```

```
<210> SEQ ID NO 2
<211> LENGTH: 31
<212> TYPE: DNA
<213> ORGANISM: Artificial Sequence
<220> FEATURE:
<223> OTHER INFORMATION: Synthetic DNA

<400> SEQUENCE: 2
tgatgcctct tcacattgct ccacctttcc t                                    31

<210> SEQ ID NO 3
<211> LENGTH: 21
<212> TYPE: DNA
<213> ORGANISM: Artificial Sequence
<220> FEATURE:
<223> OTHER INFORMATION: Synthetic DNA

<400> SEQUENCE: 3
ggatctagcc gtgtgcccgc t                                               21

<210> SEQ ID NO 4
<211> LENGTH: 24
<212> TYPE: DNA
<213> ORGANISM: Artificial Sequence
<220> FEATURE:
<223> OTHER INFORMATION: Synthetic DNA

<400> SEQUENCE: 4
ggcatggagg ttgtcccatt tgtg                                            24

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA

<400> SEQUENCE: 5
atctagccgt gtgcccgctt                                                 20

<210> SEQ ID NO 6
<211> LENGTH: 25
<212> TYPE: DNA
<213> ORGANISM: Artificial Sequence
<220> FEATURE:
<223> OTHER INFORMATION: Synthetic DNA

<400> SEQUENCE: 6
ggttgtccca tttgtggagg acagc                                           25

<210> SEQ ID NO 7
<211> LENGTH: 3150
<212> TYPE: DNA
<213> ORGANISM: Artificial Sequence
<220> FEATURE:
<223> OTHER INFORMATION: Synthetic DNA

<400> SEQUENCE: 7
tcgttgggaa ccggagctga atgaagccat accaaacgac gagcgtgaca ccacgatgcc    60
```

-continued

```
tgtagcaatg gcaacaacgt tgcgcaaact attaactggc gaactactta ctctagcttc      120
ccggcaacaa ttaatagact ggatggaggc ggataaagtt gcaggaccac ttctgcgctc      180
ggcccttccg gctggctggt ttattgctga taaatctgga gccggtgagc gtggttctcg      240
cggtatcatt gcagcactgg ggccagatgg taagccctcc cgtatcgtag ttatctacac      300 gacgggagt caggcaacta tggatgaacg aaatagacag atcgctgaga taggtgcctc       360
actgattaag cattggtaac tgtcagacca agtttactca tatatacttt agattgattt      420
aaaacttcat ttttaattta aaaggatcta ggtgaagatc cttttttgata atctcatgac     480 caaaatccct taacgtgagt tttcgttcca ctgagcgtca gaccccgtag aaaagatcaa      540
aggatcttct tgagatcctt ttttttctgcg cgtaatctgc tgcttgcaaa caaaaaaacc     600
accgctacca gcggtggttt gtttgccgga tcaagagcta ccaactcttt ttccgaaggt      660
aactggcttc agcagagcgc agataccaaa tactgttctt ctagtgtagc cgtagttagg      720
ccaccacttc aagaactctg tagcaccgcc tacatacctc gctctgctaa tcctgttacc      780
agtggctgct gccagtggcg ataagtcgtg tcttaccggg ttggactcaa gacgatagtt      840
accggataag gcgcagcggt cgggctgaac ggggggttcg tgcacacagc ccagcttgga      900
gcgaacgacc tacaccgaac tgagatacct acagcgtgag ctatgagaaa gcgccacgct      960
tcccgaaggg agaaaggcgg acaggtatcc ggtaagcggc agggtcggaa caggagagcg     1020
cacgagggag cttccagggg gaaacgcctg gtatctttat agtcctgtcg ggtttcgcca     1080
cctctgactt gagcgtcgat ttttgtgatg ctcgtcaggg gggcggagcc tatggaaaaa     1140
cgccagcaac gcggcctttt tacggttcct ggccttttgc tggccttttg ctcacatgtt     1200
ctttcctgcg ttatcccctg attctgtgga taaccgtatt accgcctttg agtgagctga     1260
taccgctcgc cgcagccgaa cgaccgagcg cagcgagtca gtgagcgagg aagcggaaga     1320
gcgcccaata cgcaaaccgc ctctccccgc gcgttggccg attcattaat gcagctggca     1380
cgacaggttt cccgactgga aagcgggcag tgagcgcaac gcaattaatg tgagttagct     1440
cactcattag gcaccccagg ctttacactt tatgcttccg gctcgtatgt tgtgtggaat     1500
tgtgagcgga taacaatttc acacaggaaa cagctatgac catgattacg ccaagcttgg     1560
atcctatctc ctttcgaaag ttgagaccat ggaattcact ggccgtcgtt ttacaacgtc     1620
gtgactggga aaaccctggc gttacccaac ttaatcgcct tgcagcacat ccccctttcg     1680
ccagctggcg taatagcgaa gaggcccgca ccgatcgccc ttcccaacag ttgcgcagcc     1740
tgaatggcga atgcgcctg atgcggtatt ttctccttac gcatctgtgc ggtatttcac      1800
accgcatacg tcaaagcaac catagtacgc gccctgtagc ggcgcattaa gcgcggcggg     1860
tgtggtggtt acgcgcagcg tgaccgctac acttgccagc gccctagcgc ccgctccttt     1920
cgctttcttc ccttcctttc tcgccacgtt cgccggcttt cccgtcaag ctctaaatcg      1980 ggggctccct ttagggttcc gatttagtgc tttacggcac ctcgacccca aaaaacttga     2040
tttgggtgat ggttcacgta gtgggccatc gccctgatag acggtttttc gccctttgac     2100
gttggagtcc acgttcttta atagtggact cttgttccaa actggaacaa cactcaaccc     2160
tatctcgggc tattcttttg atttataagg gattttgccg atttcggcct attggttaaa     2220
aaatgagctg atttaacaaa aatttaacgc gaattttaac aaaatattaa cgtttacaat     2280
tttatggtgc actctcagta caatctgctc tgatgccgca tagttaagcc agccccgaca     2340
cccgccaaca cccgctgacg cgccctgacg ggcttgtctg ctcccggcat ccgcttacag     2400
acaagctgtg accgtcaacg ggagctgcat gtgtcagagg ttttcaccgt catcaccgaa     2460
```

```
acgcgcgacc cgaaaggggcc tcgtgatacg cctattttta taggttaatg tcatgataat    2520
aatggtttct tagacgtcag gtggcacttt tcggggaaat gtgcgcggaa ccccctatttg    2580 tttattttc  taaatacatt caaatatgta tccgctcatg agacaataac cctgataaat    2640
gcttcaataa tattgaaaaa ggaagagtat gagtattcaa catttccgtg tcgcccttat    2700
tccctttttt gcggcatttt gccttcctgt ttttgctcac ccagaaacgc tggtgaaagt    2760
aaaagatgct gaagatcagt tgggtgcacg agtgggttac atcgaactgg atctcaacag    2820
cggtaagatc cttgagagtt ttcgccccga agaacgtttt ccaatgatga gcacttttaa    2880
agttctgcta tgtggcgcgg tattatcccg tattgacgcc gggcaagagc aactcggtcg    2940
ccgcatacac tattctcaga atgacttggt tgagtactca ccagtcacag aaaagcatct    3000
tacggatggc atgacagtaa gagaattatg cagtgctgcc ataaccatga gtgataacac    3060
tgcggccaac ttacttctga caacgatcgg aggaccgaag gagctaaccg cttttttgca    3120
caacatgggg gatcatgtaa ctcgccttga                                     3150

<210> SEQ ID NO 8
<211> LENGTH: 3350
<212> TYPE: DNA
<213> ORGANISM: Artificial Sequence
<220> FEATURE:
<223> OTHER INFORMATION: Synthetic DNA

<400> SEQUENCE: 8 tcgtttgggaa ccggagctga atgaagccat accaaacgac gagcgtgaca ccacgatgcc     60
tgtagcaatg gcaacaacgt tgcgcaaact attaactggc gaactactta ctctagcttc    120
ccggcaacaa ttaatagact ggatggaggc ggataaagtt gcaggaccac ttctgcgctc    180
ggcccttccg gctggctggt ttattgctga taaatctgga gccggtgagc gtggttctcg    240
cggtatcatt gcagcactgg ggccagatgg taagccctcc cgtatcgtag ttatctacac    300
gacggggagt caggcaacta tggatgaacg aaatagacag atcgctgaga taggtgcctc    360
actgattaag cattggtaac tgtcagacca agtttactca tatatacttt agattgattt    420
aaaacttcat ttttaattta aaaggatcta ggtgaagatc ctttttgata atctcatgac    480
caaaatccct taacgtgagt tttcgttcca ctgagcgtca gaccccgtag aaaagatcaa    540
aggatcttct tgagatcctt ttttttctgcg cgtaatctgc tgcttgcaaa caaaaaaacc    600
accgctacca gcggtggttt gtttgccgga tcaagagcta ccaactcttt ttccgaaggt    660
aactggcttc agcagagcgc agataccaaa tactgttctt ctagtgtagc cgtagttagg    720
ccaccacttc aagaactctg tagcaccgcc tacatacctc gctctgctaa tcctgttacc    780
agtggctgct gccagtggcg ataagtcgtg tcttaccggg ttggactcaa gacgatagtt    840
accggataag gcgcagcggt cgggctgaac ggggggttcg tgcacacagc ccagcttgga    900
gcgaacgacc tacaccgaac tgagatacct acagcgtgag ctatgagaaa gcgccacgct    960
tcccgaaggg agaaaggcgg acaggtatcc ggtaagcggc agggtcggaa caggagagcg   1020
cacgagggag cttccagggg gaaacgcctg gtatctttat agtcctgtcg ggtttcgcca   1080
cctctgactt gagcgtcgat ttttgtgatg ctcgtcaggg gggcggagcc tatggaaaaa   1140
cgccagcaac gcggcctttt tacggttcct ggccttttgc tggccttttg ctcacatgtt   1200
ctttcctgcg ttatccctg attctgtgga taaccgtatt accgcctttg agtgagctga   1260
taccgctcgc cgcagccgaa cgaccgagcg cagcgagtca gtgagcgagg aagcggaaga   1320
```

```
gcgcccaata cgcaaaccgc ctctcccgc gcgttggccg attcattaat gcagctggca    1380
cgacaggttt cccgactgga aagcgggcag tgagcgcaac gcaattaatg tgagttagct    1440
cactcattag gcaccccagg ctttacactt tatgcttccg gctcgtatgt tgtgtggaat    1500
tgtgagcgga taacaatttc acacaggaaa cagctatgac catgattacg ccaagcttgg    1560
atcctatctc ctttcgatgc tcccttcggc atccattaac ctggcactca ccttgcgtat    1620
agcaggatct agccgtgtgc ccgcttcgca ggcaattgaa gcagagctga tgcctcttca    1680
cattgctcca ccttttcctgt ggcgaagctc caataaattt tctgcagttc aatatttcat    1740
gctgtcctcc acaaatggga caacctccat gccgagaaag ttgagaccat ggaattcact    1800
ggccgtcgtt ttacaacgtc gtgactggga aaaccctggc gttacccaac ttaatcgcct    1860
tgcagcacat ccccctttcg ccagctggcg taatagcgaa gaggcccgca ccgatcgccc    1920
ttcccaacag ttgcgcagcc tgaatggcga atggcgcctg atgcggtatt ttctccttac    1980
gcatctgtgc ggtatttcac accgcatacg tcaaagcaac catagtacgc gccctgtagc    2040
ggcgcattaa gcgcggcggg tgtggtggtt acgcgcagcg tgaccgctac acttgccagc    2100
gccctagcgc ccgctccttt cgctttcttc ccttcctttc tcgccacgtt cgccggcttt    2160
ccccgtcaag ctctaaatcg ggggctccct ttagggttcc gatttagtgc tttacggcac    2220
ctcgacccca aaaaacttga tttgggtgat ggttcacgta gtgggccatc gccctgatag    2280 acggttttc gcccttttgac gttggagtcc acgttcttta atagtggact cttgttccaa    2340
actggaacaa cactcaaccc tatctcgggc tattcttttg atttataagg gattttgccg    2400
atttcggcct attggttaaa aaatgagctg atttaacaaa aatttaacgc gaattttaac    2460
aaaatattaa cgtttacaat tttatggtgc actctcagta caatctgctc tgatgccgca    2520
tagttaagcc agccccgaca cccgccaaca cccgctgacg cgccctgacg gcttgtctg    2580 ctcccggcat ccgcttacag acaagctgtg accgtcaacg ggagctgcat gtgtcagagg    2640
ttttcaccgt catcaccgaa acgcgcgacc cgaaagggcc tcgtgatacg cctatttta    2700 taggttaatg tcatgataat aatggtttct tagacgtcag gtggcacttt tcggggaaat    2760
gtgcgcggaa cccctatttg tttatttttc taaatacatt caaatatgta tccgctcatg    2820
agacaataac cctgataaat gcttcaataa tattgaaaaa ggaagagtat gagtattcaa    2880
catttccgtg tcgcccttat tcccttttttt gcggcatttt gccttcctgt ttttgctcac    2940
ccagaaacgc tggtgaaagt aaaagatgct gaagatcagt tgggtgcacg agtgggttac    3000
atcgaactgg atctcaacag cggtaagatc cttgagagtt ttcgccccga agaacgtttt    3060
ccaatgatga gcacttttaa agttctgcta tgtggcgcgg tattatcccg tattgacgcc    3120
gggcaagagc aactcggtcg ccgcatacac tattctcaga atgacttggt tgagtactca    3180
ccagtcacag aaaagcatct tacggatggc atgacagtaa gagaattatg cagtgctgcc    3240
ataaccatga gtgataacac tgcggccaac ttacttctga caacgatcgg aggaccgaag    3300
gagctaaccg cttttttgca acaacatgggg gatcatgtaa ctcgccttga    3350
```

<210> SEQ ID NO 9
<211> LENGTH: 149
<212> TYPE: DNA
<213> ORGANISM: Drosophila melanogaster

<400> SEQUENCE: 9

```
ggatctagcc gtgtgcccgc ttcgcaggca attgaagcag agctgatgcc tcttcacatt      60
gctccacctt tcctgtggcg aagctccaat aaattttctg cagttcaata tttcatgctg     120
```

```
tcctccacaa atgggacaac ctccatgcc                                         149
```

<210> SEQ ID NO 10
<211> LENGTH: 149
<212> TYPE: DNA
<213> ORGANISM: Drosophila melanogaster

<400> SEQUENCE: 10

```
ggatctagcc gtgtgcccgc ttcgcaggca attgaagcag agccgatgcc tcttcacatt        60
gctccacctt tcctgtggcg aagctccaat aaatttctg cagttcaata tttcatgctg        120
tcctccacaa atgggacaac ctccatgcc                                         149
```

<210> SEQ ID NO 11
<211> LENGTH: 149
<212> TYPE: DNA
<213> ORGANISM: Drosophila melanogaster

<400> SEQUENCE: 11

```
ggatctagcc gtgtgcccgc ttcgcaggca attgaagcag agccgatgcc tcttcacatt        60
gctccacctt tcctgtggcg aagctccaat aaatttctg cagttcaata tttcatgctg        120
tcctccacag atgggacaac ctccatgcc                                         149
```

<210> SEQ ID NO 12
<211> LENGTH: 149
<212> TYPE: DNA
<213> ORGANISM: Drosophila melanogaster

<400> SEQUENCE: 12

```
ggatctagcc gtgtgcccgc ttcgcaggca attgaagcag agccgatgcc tcttcacatt        60
gctccacctt tcctgtgccg aagctccaat aaatttctg cagttcaata tttcatgctg        120
tcctccacag atgggacaac ctccatgcc                                         149
```

<210> SEQ ID NO 13
<211> LENGTH: 149
<212> TYPE: DNA
<213> ORGANISM: Drosophila melanogaster

<400> SEQUENCE: 13

```
ggatctagcc gtgtgcccgc ttcgcaggca attgaagcag agccgatgcc tcttcacatt        60
gctccacctt tcctgtgccg aagctccaat aaatttctg cagttcaata tttcatgctg        120
tcctccacag atgggacaac ctccatgcc                                         149
```

<210> SEQ ID NO 14
<211> LENGTH: 200
<212> TYPE: DNA
<213> ORGANISM: Drosophila melanogaster

<400> SEQUENCE: 14

```
gatgctccct tcggcatcca ttaacctggc actcaccttg cgtatagcag gatctagccg        60
tgtgcccgct tcgcaggcaa ttgaagcaga gccgatgcct cttcacattg ctccaccttt       120
cctgtggcga agctccaata aatttctgc agttcaatat ttcatgctgt cctccacaaa       180
tgggacaacc tccatgccga                                                   200
```

<210> SEQ ID NO 15
<211> LENGTH: 3350
<212> TYPE: DNA

<210> ORGANISM: Artificial Sequence
<220> FEATURE:
<223> OTHER INFORMATION: Synthetic DNA

<400> SEQUENCE: 15

```
tcgttgggaa ccggagctga atgaagccat accaaacgac gagcgtgaca ccacgatgcc      60
tgtagcaatg gcaacaacgt tgcgcaaact attaactggc gaactactta ctctagcttc     120
ccggcaacaa ttaatagact ggatggaggc ggataaagtt gcaggaccac ttctgcgctc     180
ggcccttccg gctggctggt ttattgctga taaatctgga gccggtgagc gtggttctcg     240
cggtatcatt gcagcactgg ggccagatgg taagccctcc cgtatcgtag ttatctacac     300
gacggggagt caggcaacta tggatgaacg aaatagacag atcgctgaga taggtgcctc     360
actgattaag cattggtaac tgtcagacca agtttactca tatatacttt agattgattt     420
aaaacttcat ttttaattta aaaggatcta ggtgaagatc ctttttgata atctcatgac     480
caaaatccct taacgtgagt tttcgttcca ctgagcgtca gaccccgtag aaaagatcaa     540
aggatcttct tgagatcctt ttttctgcg cgtaatctgc tgcttgcaaa caaaaaaacc     600
accgctacca gcggtggttt gtttgccgga tcaagagcta ccaactcttt ttccgaaggt     660
aactggcttc agcagagcgc agataccaaa tactgttctt ctagtgtagc cgtagttagg     720
ccaccacttc aagaactctg tagcaccgcc tacatacctc gctctgctaa tcctgttacc     780
agtggctgct gccagtggcg ataagtcgtg tcttaccggg ttggactcaa gacgatagtt     840
accggataag gcgcagcggt cgggctgaac ggggggttcg tgcacacagc ccagcttgga     900
gcgaacgacc tacaccgaac tgagatacct acagcgtgag ctatgagaaa gcgccacgct     960
tcccgaaggg agaaaggcgg acaggtatcc ggtaagcggc agggtcggaa caggagagcg    1020
cacgaggag cttccagggg gaaacgcctg gtatctttat agtcctgtcg ggtttcgcca    1080
cctctgactt gagcgtcgat ttttgtgatg ctcgtcaggg gggcggagcc tatggaaaaa    1140
cgccagcaac gcggcctttt tacggttcct ggccttttgc tggccttttg ctcacatgtt    1200
ctttcctgcg ttatccctg attctgtgga taaccgtatt accgcctttg agtgagctga    1260
taccgctcgc cgcagccgaa cgaccgagcg cagcgagtca gtgagcgagg aagcggaaga    1320
gcgcccaata cgcaaaccgc ctctccccgc gcgttggccg attcattaat gcagctggca    1380
cgacaggttt cccgactgga aagcgggcag tgagcgcaac gcaattaatg tgagttagct    1440
cactcattag gcaccccagg ctttacactt tatgcttccg gctcgtatgt tgtgtggaat    1500
tgtgagcgga taacaatttc acacaggaaa cagctatgac catgattacg ccaagcttgg    1560
atcctatctc ctttcgatgc tcccttcggc atccattaac ctggcactca ccttgcgtat    1620
agcaggatct agccgtgtgc ccgcttcgca ggcaattgaa gcagagccga tgcctcttca    1680
cattgctcca cctttcctgt ggcgaagctc aataaatttt tctgcagttc aatatttcat    1740
gctgtcctcc acaaatggga caacctccat gccgagaaag ttgagaccat ggaattcact    1800
ggccgtcgtt ttacaacgtc gtgactggga aaaccctggc gttacccaac ttaatcgcct    1860
tgcagcacat ccccctttcg ccagctggcg taatagcgaa gaggcccgca ccgatcgccc    1920
ttcccaacag ttgcgcagcc tgaatggcga atggcgcctg atgcggtatt ttctccttac    1980
gcatctgtgc ggtatttcac accgcatacg tcaaagcaac catagtacgc gccctgtagc    2040
ggcgcattaa gcgcggcggg tgtggtggtt acgcgcagcg tgaccgctac acttgccagc    2100
gccctagcgc ccgctccttt cgctttcttc ccttcctttc tcgccacgtt cgccggcttt    2160
ccccgtcaag ctctaaatcg gggggctccct ttagggttcc gatttagtgc tttacggcac    2220
```

-continued

```
ctcgacccca aaaaacttga tttgggtgat ggttcacgta gtgggccatc gccctgatag    2280 acggttttc gccctttgac gttggagtcc acgttcttta atagtggact cttgttccaa     2340
actggaacaa cactcaaccc tatctcgggc tattcttttg atttataagg gattttgccg    2400
atttcggcct attggttaaa aaatgagctg atttaacaaa aatttaacgc gaattttaac    2460
aaaatattaa cgtttacaat tttatggtgc actctcagta caatctgctc tgatgccgca    2520
tagttaagcc agccccgaca cccgccaaca cccgctgacg cgccctgacg ggcttgtctg    2580
ctcccggcat ccgcttacag acaagctgtg accgtcaacg ggagctgcat gtgtcagagg    2640
ttttcaccgt catcaccgaa acgcgcgacc cgaaagggcc tcgtgatacg cctatttta    2700 taggttaatg tcatgataat aatggtttct tagacgtcag gtggcacttt tcggggaaat    2760
gtgcgcggaa cccctatttg tttattttc taaatacatt caaatatgta tccgctcatg    2820
agacaataac cctgataaat gcttcaataa tattgaaaaa ggaagagtat gagtattcaa    2880
catttccgtg tcgcccttat tccctttttt gcggcatttt gccttcctgt ttttgctcac    2940
ccagaaacgc tggtgaaagt aaaagatgct gaagatcagt tgggtgcacg agtgggttac    3000
atcgaactgg atctcaacag cggtaagatc cttgagagtt ttcgccccga agaacgtttt    3060
ccaatgatga gcacttttaa agttctgcta tgtggcgcgg tattatcccg tattgacgcc    3120
gggcaagagc aactcggtcg ccgcatacac tattctcaga atgacttggt tgagtactca    3180
ccagtcacag aaaagcatct tacggatggc atgacagtaa gagaattatg cagtgctgcc    3240
ataaccatga gtgataacac tgcggccaac ttacttctga caacgatcgg aggaccgaag    3300
gagctaaccg cttttttgca caacatgggg gatcatgtaa ctcgccttga              3350
```

<210> SEQ ID NO 16
<211> LENGTH: 32
<212> TYPE: DNA
<213> ORGANISM: Artificial Sequence
<220> FEATURE:
<223> OTHER INFORMATION: Synthetic DNA

<400> SEQUENCE: 16

```
ttgatgcctc ttcacattgc tccacctttc ct                                    32
```

INTERNAL CONTROL NUCLEIC ACIDS FOR AMPLIFICATION

CROSS-REFERENCE TO RELATED APPLICATIONS

This application is a divisional of U.S. application Ser. No. 14/388,704 filed Sep. 26, 2014, which is the national phase of PCT App. No. PCT/US2013/031032, filed Mar. 13, 2013, which claims priority to U.S. Provisional Patent Application No. 61/617,562, filed Mar. 29, 2012, each of which is hereby incorporated by reference in its entirety.

REFERENCE TO SEQUENCE LISTING

The present application is being filed along with a Sequence Listing in electronic format. The Sequence Listing is provided as a file entitled REPLACEMENT_PCT_SEQLIST_GENOM_115WO.TXT, created and last saved on Mar. 26, 2013, which is 15,655 bytes in size. The information is incorporated herein by reference in its entirety.

FIELD

Embodiments herein relate generally to internal control nucleic acids that are useful in monitoring nucleic acid amplification and/or extraction from samples in nucleic acid testing (NAT).

BACKGROUND

Nucleic acid testing (NAT) assays provide powerful tools for the rapid detection and/or quantification of target nucleic acids. As such, NAT assays are commonly used to detect the presence of organisms in a sample, e.g., in patient samples in a clinical setting, in food samples, in environmental samples and the like. NAT assays are also commonly used in diagnostic settings, e.g., to detect genetic polymorphisms, genetic repeats, insertions, deletions, or the like, or altered gene expression, as indicative of a condition such as a disease or disorder.

In many situations, it is desirable to obtain quantitative information regarding the amount of a target nucleic acid sequence in a given sample. For example, quantitative nucleic acid assays, e.g., amplification assays, can be used to detect the presence and/or amount of a pathogen-specific target sequence present in a biological sample to determine whether the sample is infected with the pathogen, and/or to monitor the progression or severity of the infection. Quantitative nucleic acid assays can also be useful for monitoring the state of a cell or tissue by monitoring the amount of a marker nucleic acid sequence present in the cell or tissue, or for quantifying the amount of a specific DNA element, for example a repeat or a transposable element, present in a sample.

Quantitative nucleic acid amplification reactions can be used for quantifying the relative and/or absolute amount of target nucleic acid sequences present in a sample. Such methods have become highly advanced and sensitive, such that only a few copies of target nucleic acid can be detected in a sample. Due to the highly sensitive nature of quantitative nucleic acid amplification reactions, in order to avoid false positives, false negatives, overestimation of target or product quantity, or underestimation of target or product quantity, extreme care must be taken when choosing appropriate internal controls. In addition to considerations regarding the specificity of internal controls (e.g., internal control templates, primers and/or probes), considerations regarding intrinsic features of control nucleic acid sequences, including, e.g., hairpins, A/T runs with very low annealing temperatures, G/C runs with very high annealing temperatures that do not make the nucleic acids amenable to amplification and/or probe hybridization exist. Additionally, it may be desirable to use the same internal control template sequence, primer set, and probe in a variety of multiplex reactions, for a variety of target sequences. However, many nucleic acid sequences are amenable to amplification and/or probe hybridization under a narrow set of reaction conditions, and are not sufficiently robust to be used as internal controls under a wide variety of reaction conditions.

Thus, one skilled in the art will appreciate the complicated nature of identifying a robust combination of an internal control sequence, primers, and probes for performing an internal control to monitor nucleic acid amplification. Moreover, one skilled in the art will appreciate that extensive empirical validation is often performed to verify that a polynucleotide template sequence, primer pair, probe, or combination thereof will function as a viable/adequate internal control for quantitative nucleic acid amplification.

SUMMARY

The embodiments disclosed herein relate to improved compositions useful as internal controls for nucleic acid testing (NAT) assays. Accordingly, provided herein are internal control reagents, kits containing the internal control reagents, as well as methods of making and using the same in nucleic acid testing assays. As described in further detail below, the internal control reagents disclosed herein exhibit highly advantageous properties, including tremendous sensitivity and reproducibility. Furthermore, the internal control reagents disclosed herein are highly versatile and useful as controls in NAT assays for the detection and/or quantification of a wide array of different target sequences.

Accordingly, in some embodiments polynucleotides that can be used as templates in nucleic acid amplification reactions, including but not limited to quantitative and/or qualitative nucleic acid amplification reactions, are provided. In some embodiments, the polynucleotides can be used as internal control templates for quantitative nucleic acid testing assays, such as quantitative PCR. Exemplary internal control template polynucleotides comprise, consist essentially of, or consist of the sequence of SEQ ID NOs: 1, 8, 9, 10, 11, 12, 13, 14, or 15 or variants thereof including subsequences thereof.

In some embodiments, oligonucleotides that can be used as primers for nucleic acid amplification, e.g., to amplify template control sequences used as standards and/or internal controls, are provided. The oligonucleotides can include individual primers and/or primer pairs for nucleic acid amplification. In some embodiments, the primers can be used to amplify a control template sequence (e.g. SEQ ID NOs: 1, 8, 9, 10, 11, 12, 13, 14, 15, and variants thereof, including subsequences thereof). Exemplary primers comprise, consist essentially of, or consist of the sequence of SEQ ID NOs: 3, 4, 5, or 6, or variants thereof.

In some embodiments, oligonucleotides that can be used as probes are provided. In some embodiments, the probes comprise oligonucleotides that can hybridize to amplicons of control sequences disclosed herein, e.g., SEQ ID NOs: 1, 8, 9, 10, 11, 12, 13, 14, 15 and variants thereof). Exemplary probes comprise, consist essentially of, or consist of the sequence of SEQ ID NO: 2, or variants thereof.

In some embodiments, kits are provided. Kits can include polynucleotides and/or oligonucleotides as described herein. In some embodiments, kits can include polynucleotides and/or oligonucleotides for a quantitative for nucleic acid amplification internal control. The kits can include at least one of a polynucleotide template, a primer that specifically amplifies template sequences. In some embodiments, the kit can include an amplification primer pair that specifically amplifies template sequences. In some embodiments, the kits can optionally include a probe that specifically hybridizes to the polynucleotide template. The kits disclosed herein can optionally include a polymerase, a reaction buffer, one or more dNTPs, or any combination thereof, as well as other reagents used in amplification reactions.

Some embodiments provide methods of performing an NAT assay. In some embodiments, the method includes providing a polynucleotide template sequence comprising, consisting essentially of, or consisting of SEQ ID NO:1, and contacting the template sequence with at least one primer, e.g., a primer of SEQ ID NO: 3, 4, 5, or 6, that specifically hybridizes to the template sequence. In some embodiments, the polynucleotide includes a variant of SEQ ID NO: 1. In some embodiments, the method includes extending the primer, thus producing an amplicon of the template sequence. In some embodiments, the method includes detecting the presence and/or amount of the amplicon. In some embodiments, the detecting step comprises contacting the amplicon with a probe, wherein the probe comprises a detectable moiety and wherein the probe binds to the amplicon. In some embodiments, the method includes the step of determining the amount of probe that is specifically bound to an amplicon. In some embodiments, the determining step is performed in real time as the amplicons are generated. In some embodiments, the probe comprises a detectable moiety, and the amount of signal from the detectable moiety is measured. In some embodiments, the accumulation of probe that is specifically hybridized to or bound to the amplicons is measured as a function of time or cycle and an amplification curve is generated. In some embodiments, a series of reactions are performed, wherein in each reaction, a different, known amount of template sequence is provided. In some embodiments, the method includes the step of generating a standard curve from a series of amplification curves. In some embodiments, the standard curve is used to determine the initial concentration of a polynucleotide sequence in an amplification reaction. In some embodiments, the amplification reactions comprise multiplex amplification reactions.

BRIEF DESCRIPTION OF THE DRAWINGS

FIGS. 2A and 2B show the sequence of a modified PUC 119 vector (FIG. 2A shows positions 1-1800 of the sequence, and FIG. 2B shows positions 1801-3350 of the sequence) containing an insert that includes an exemplary internal control template sequence ("DrosScaff2"; SEQ ID NO: 8), and the relative positions of primers comprising SEQ ID NO: 3 and SEQ ID NO: 4, and a probe comprising SEQ ID NO: 2. As noted by a diamond symbol, the "t" residue at position 1668 of this sequence differ from the "C" residues found at the corresponding position in SEQ ID NO: 15 ("DrosScaff1").

FIG. 4A shows amplification curves (fluorescence versus cycle) of a series of amplification reactions wherein the initial template concentration was 200, 50, 25, or 5 copies of linearized plasmid comprising SEQ ID NO: 8, and wherein the primers of Primer Pair 5 were used as the amplification primers. A fluorescent probe comprising the sequence of SEQ ID NO: 2 was used in the reactions.

FIG. 4B shows amplification curves (fluorescence versus cycle) of a series of real-time amplification reactions wherein the initial template concentration was 200, 50, 25, or 5 copies of linearized plasmid comprising SEQ ID NO: 8, and wherein the primers of Primer Pair 1 were used as the amplification primers. A fluorescent probe comprising the sequence of SEQ ID NO:2 was used in the reactions.

FIG. 4C shows amplification curves (fluorescence versus cycle) of a series of real-time amplification reactions wherein the initial template concentration was 200, 50, 25, or 5 copies of linearized plasmid comprising SEQ ID NO: 8, and wherein the primers of Primer Pair 5 were used as the amplification primers. A fluorescent probe comprising the sequence of SEQ ID NO:2 was used in the reactions.

FIG. 4D shows amplification curves (fluorescence versus cycle) of a series of real-time amplification reactions wherein the initial template concentration was 200, 50, 25, and 5 copies of linearized plasmid comprising SEQ ID NO: 8, and wherein the primers of Primer Pair 5 were used as the amplification primers. A fluorescent probe comprising the sequence of SEQ ID NO:2 was used in the reactions.

FIG. 5 illustrates PCR performance (PCR Efficiency, R2 and Slope) and sensitivity, detecting as few as 5 copies/reaction of linearized plasmid ("DrosScaff1" plasmid) having the sequence of SEQ ID NO: 15.

DETAILED DESCRIPTION

Figure 1:
FIG. 1 illustrates a vector map of a modified PUC 119 vector having the sequence of SEQ ID NO: 8.

It is to be understood that both the foregoing general description and the following detailed description are exemplary and explanatory only and are not intended to limit the scope of the current teachings. In this application, the use of the singular includes the plural unless specifically stated otherwise. Also, the use of "comprise", "contain", and "include", or modifications of those root words, for example but not limited to, "comprises", "contained", and "including", are not intended to be limiting. Use of "or" means "and/or" unless stated otherwise. The term "and/or" means that the terms before and after can be taken together or separately. For illustration purposes, but not as a limitation, "X and/or Y" can mean "X" or "Y" or "X and Y".

Whenever a range of values is provided herein, the range is meant to include the starting value and the ending value and any value or value range there between unless otherwise specifically stated. For example, "from 0.2 to 0.5" means 0.2, 0.3, 0.4, 0.5; ranges there between such as 0.2-0.3, 0.3-0.4, 0.2-0.4; increments there between such as 0.25, 0.35, 0.225, 0.335, 0.49; increment ranges there between such as 0.26-0.39; and the like.

The section headings used herein are for organizational purposes only and are not to be construed as limiting the subject matter described in any way. All literature and similar materials cited in this application including, but not limited to, patents, patent applications, articles, books, treatises, and internet web pages, regardless of the format of such literature and similar materials, are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Various embodiments of this disclosure describe compositions, and kits, and methods of using the same, for use in nucleic acid testing (NAT) assays. Accordingly, some embodiments provide nucleic acid sequences for use in NAT assays, e.g., in amplification assays. A person skilled in the art will appreciate that for any nucleic acid sequence, the reverse compliment can be readily obtained, and that a disclosure of a nucleic acid sequence also provides a disclosure of the reverse compliment of that sequence. A person skilled in the art will appreciate that subsequences of the nucleic sequences disclosed herein can be readily obtained.

The nucleic acids provided herein can be in various forms. For example, in some embodiments, the nucleic acids are dissolved (either alone or in combination with various other nucleic acids) in solution, for example buffer. In some embodiments, nucleic acids are provided, either alone or in combination with other isolated nucleic acids, as a salt. In some embodiments, nucleic acids are provided in a lyophilized form that can be reconstituted. For example, in some embodiments, the isolated nucleic acids disclosed herein can be provided in a lyophilized pellet alone, or in a lyophilized pellet with other isolated nucleic acids. In some embodiments, nucleic acids are provided affixed to a solid substance, such as a bead, a membrane, or the like. In some embodiments, nucleic acids are provided in a host cell, for example a cell line carrying a plasmid, or a cell line carrying a stably integrated sequence.

Control Sequences

Some embodiments disclosed herein provide control nucleic acid sequences for NAT assays. In some embodiments, the control sequence can be used as an external control, or standard, that is processed in parallel with test samples. In some embodiments, the control sequence can be used as an internal control and is combined with the test sample prior to processing.

The skilled artisan will appreciate that the term "nucleic acid" encompasses polydeoxyribonucleotides (containing 2-deoxy-D-ribose), polyribonucleotides (containing D-ribose), as well as any other type of polynucleotide which is an N- or C-glycoside of a purine or pyrimidine base, and to other polymers containing non-nucleotidic backbones, for example, polyamide (e.g., peptide nucleic acids (PNAs)) and polymorpholino (commercially available from the Anti-Virals, Inc., Corvallis, Oreg., as NEUGENE™ polymers), and other synthetic sequence-specific nucleic acid polymers providing that the polymers contain nucleobases in a configuration which allows for base pairing and base stacking, such as is found in DNA and RNA.

The terms nucleotide and polynucleotide include, for example, 3'-deoxy-2',5'-DNA, oligodeoxyribonucleotide N3'→P5' phosphoramidates, 2'-O-alkyl-substituted RNA, double- and single-stranded DNA, as well as double- and single-stranded RNA, DNA:RNA hybrids, and hybrids between PNAs and DNA or RNA. The terms also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides will also include modifications on the sugar moiety, e.g., wherein one or more of the hydroxyl groups are replaced with a halogen, an aliphatic group, or are functionalized as ethers, amines, or the like. Other modifications to nucleotides or polynucleotides involve rearranging, appending, substituting for, or otherwise altering functional groups on the purine or pyrimidine base which form hydrogen bonds to a respective complementary pyrimidine or purine, e.g., isoguanine, isocysteine, and the like. In some embodiments, the oligonucleotides and/or probes include at least one, two, three or four modified nucleotides.

In some embodiments, the nucleic acids disclosed herein include one or more universal bases. As used herein, the term "universal base" refers to a nucleotide analog that can hybridize to more than one nucleotide selected from A, T, C, and G. In some embodiments, the universal base can be selected from the group consisting of deoxyinosine, 3-ntiropyrrole, 4-nitroindole, 6-nitroindole, 5-nitroindole.

In some embodiments, the control nucleic acid sequences disclosed herein are target control sequences ("TCSs"), which are templates for nucleic acid amplification reactions. Those skilled in the art will appreciate that subsequences of the TCS disclosed herein can be amplified by PCR or other amplification methods as discussed in further detail herein, as can the entirety of the TCS's disclosed herein. In some embodiments, a TCS is provided as a control for a multiplex assay, in which a known quantity of TCS and at least one target nucleic acid to-be-quantified are each amplified in the same reaction mixture. In some embodiments, a known quantity of TCS is amplified in a first reaction mixture, while a target nucleic acid to-be-quantified is amplified in a second reaction mixture.

In some embodiments, the TCS consists of, consists essentially of, or comprises the sequence of SEQ ID NO: 1, or a variant thereof. In some embodiments, the TCS is provided in a vector, for example a plasmid. Accordingly, some embodiments provide a polynucleotide sequence that consists of, consists essentially of, or comprises SEQ ID NO:1 in a plasmid, e.g., sequences that consist of, consist essentially of, or comprise SEQ ID NO: 8. In embodiments wherein the TCS is provided in a plasmid, the plasmid can be linearized, or alternately, the plasmid can be non-linearized (e.g., in a supercoiled or unwound circular form). In some embodiments, the template sequence comprises a polynucleotide comprising at least one of the sequences of SEQ ID NOs: 9, 10, 11, 12, or 13 or a variant thereof. "Variants" of the sequences disclosed herein are discussed below.

In some embodiments, the TCS comprises isolated polynucleotides from genomic DNA, or a genomic fragment, or a modification thereof of an organism of the genus *Drosophila*, for example *Drosophila melanogaster, Drosophila simulans, Drosophila sechellia, Drosophila yakuba, Drosophila erecta, Drosophila ficusphila, Drosophila eugracilis, Drosophila biarmipes, Drosophila takahashii, Drosophila elegans, Drosophila rhopaloa, Drosophila kikkawai, Drosophila ananassae, Drosophila bipectinata, Drosophila pseudoobscura, Drosophila persimilis,* or *Drosophila willistoni*. Preferably, the TCS sequences comprises, consists of, or consists essentially of SEQ ID NO: 1 or SEQ ID NO: 14. For example, SEQ ID NO: 14 corresponds generally to sequence found in the *Drosophila melanogaster* genome (GenBank: AC246436; nucleotides 35779 to 35978), and SEQ ID NO: 1 includes a modification to SEQ ID NO: 14: the "C" residue at position 93 of SEQ ID NO: 14 was changed to a "T" at the same position of SEQ ID NO: 1. This modification, which is also found in the plasmid of SEQ ID NO: 8 is noted by a diamond symbol in FIG. 2.

Oligonucleotides

In some embodiments, oligonucleotides are provided, for example primers and/or probes. As used herein, the terms "primer" and "probe" include, but are not limited to oligonucleotides. Preferably, the oligonucleotide primers and/or probes disclosed herein can be between 8 and 45 nucleotides in length. For example, the primers and or probes can be at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more nucleotides in length. Primers and/or probes can be provided in any suitable form, included bound to a solid support, liquid, and lyophilized, for example. The primer and probe sequences disclosed herein can be modified to contain additional nucleotides at the 5' or the 3' terminus, or both. The skilled artisan will appreciate, however, that additional bases to the 3' terminus of amplification primers (not necessarily probes) are generally complementary to the template sequence. The primer and probe sequences disclosed herein can also be modified to remove nucleotides at the 5' or the 3' terminus. The skilled artisan will appreciate that in order to function for amplification, the primers or probes will be of a minimum length and annealing temperature as disclosed herein.

Oligonucleotide primers and probes can bind to their targets at an annealing temperature, which is a temperature less than the melting temperature ($T_m$). As used herein, "$T_m$" and "melting temperature" are interchangeable terms which refer to the temperature at which 50% of a population of double-stranded polynucleotide molecules becomes dissociated into single strands. Formulae for calculating the $T_m$ of polynucleotides are well known in the art. For example, the $T_m$ may be calculated by the following equation: $T_m=69.3+0.41\times(G+C)\%-6-50/L$, wherein L is the length of the probe in nucleotides. The $T_m$ of a hybrid polynucleotide may also be estimated using a formula adopted from hybridization assays in 1 M salt, and commonly used for calculating $T_m$ for PCR primers: [(number of A+T)×2° C.+(number of G+C)×4° C.]. See, e.g., C. R. Newton et al. PCR, 2nd Ed., Springer-Verlag (New York: 1997), p. 24. Other more sophisticated computations exist in the art, which take structural as well as sequence characteristics into account for the calculation of $T_m$. The melting temperature of an oligonucleotide can depend on complementarity between the oligonucleotide primer or probe and the binding sequence, and on salt conditions. In some embodiments, an oligonucleotide primer or probe provided herein has a $T_m$ of less than about 90° C. in 50 mM KCl, 10 mM Tris-HCl buffer, for example about 89° C., 88, 87, 86, 85, 84, 83, 82, 81, 80 79, 78, 77, 76, 75, 74, 73, 72, 71, 70, 69, 68, 67, 66, 65, 64, 63, 62, 61, 60, 59, 58, 57, 56, 55, 54, 53, 52, 50, 49, 48, 47, 46, 45, 44, 43, 42, 41, 40, 39° C., or less, including ranges between any two of the listed values. As discussed in further detail below, in some embodiments, the primers disclosed herein are provided as an amplification primer pair, e.g., comprising a forward primer and a reverse primer. Preferably, the forward and reverse primers have $T_m$'s that do not differ by more than 10° C., e.g., that differ by less than 10° C., less than 9° C., less than 8° C., less than 7° C., less than 6° C., less than 5° C., less than 4° C., less than 3° C., less than 2° C., or less than 1° C.

The primer and probe sequences may be modified by having nucleotide substitutions (relative to the target sequence) within the oligonucleotide sequence, provided that the oligonucleotide contains enough complementarity to hybridize specifically to the target nucleic acid sequence. In this manner, at least 1, 2, 3, 4, or up to about 5 nucleotides can be substituted. As used herein, the term "complementary" refers to sequence complementarity between regions of two polynucleotide strands or between two regions of the same polynucleotide strand. A first region of a polynucleotide is complementary to a second region of the same or a different polynucleotide if, when the two regions are arranged in an antiparallel fashion, at least one nucleotide of the first region is capable of base pairing with a base of the second region. Therefore, it is not required for two complementary polynucleotides to base pair at every nucleotide position. "Fully complementary" refers to a first polynucleotide that is 100% or "fully" complementary to a second polynucleotide and thus forms a base pair at every nucleotide position. "Partially complementary" also refers to a first polynucleotide that is not 100% complementary (e.g., 90%, or 80% or 70% complementary) and contains mismatched nucleotides at one or more nucleotide positions. In some embodiments, an oligonucleotide includes a universal base.

As used herein, the term "hybridization" is used in reference to the pairing of complementary (including partially complementary) polynucleotide strands. Hybridization and the strength of hybridization (i.e., the strength of the association between polynucleotide strands) is impacted by many factors well known in the art including the degree of complementarity between the polynucleotides, stringency of the conditions involved affected by such conditions as the concentration of salts, the melting temperature of the formed hybrid, the presence of other components (e.g., the presence or absence of polyethylene glycol), the molarity of the hybridizing strands and the G:C content of the polynucleotide strands. In some embodiments, the primers are designed such that the Tm of one primer in the set is within 2° C. of the Tm of the other primer in the set. An extensive guide to the hybridization of nucleic acids is found in Tijssen (1993) Laboratory Techniques in Biochemistry and Molecular Biology—Hybridization with Nucleic Acid Probes, Part I, Chapter 2 (Elsevier, New York); and Ausubel et al, eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, N.Y.). As discussed further herein, the term "specific hybridization" or "specifically hybridizes" refers to the hybridization of a polynucleotide, e.g., an oligonucleotide primer or probe or the like to a target sequence, such as a sequence to be quantified in a sample, a positive control target nucleic acid sequence, or the like, and not to unrelated sequences, under conditions typically used for nucleic acid amplification.

In some embodiments, the primers and/or probes include oligonucleotides that hybridize to a target nucleic acid sequence over the entire length of the oligonucleotide sequence. Such sequences can be referred to as "fully complementary" with respect to each other. Where an oligonucleotide is referred to as "substantially complementary" with respect to a nucleic acid sequence herein, the two sequences can be fully complementary, or they may form mismatches upon hybridization, but retain the ability to hybridize under stringent conditions or standard PCR conditions as discussed below. As used herein, the term "substantially complementary" refers to the complementarity between two nucleic acids, e.g., the complementary region of the oligonucleotide and the target sequence. The complementarity need not be perfect; there may be any number of base pair mismatches that between the two nucleic acids. However, if the number of mismatches is so great that no hybridization can occur under even the least stringent of hybridization conditions, the sequence is not a substantially complementary sequence. When two sequences are referred to as "substantially complementary" herein, it is meant that the sequences are sufficiently complementary to the each other to hybridize under the selected reaction conditions. The relationship of nucleic acid complementarity and stringency of hybridization sufficient to achieve specificity is well known in the art and described further below in reference to sequence identity, melting temperature and hybridization conditions. Therefore, substantially complementary sequences can be used in any of the detection methods disclosed herein. Such probes can be, for example, perfectly complementary or can contain from 1 to many mismatches so long as the hybridization conditions are sufficient to allow, for example discrimination between a target sequence and a non-target sequence. Accordingly, substantially complementary sequences can refer to sequences ranging in percent identity from 100, 99, 98, 97, 96, 95, 94, 93, 92, 91, 90, 89, 88, 87, 86, 85, 84, 83, 82, 81, 80, 75, 70 or less, or any number in between, compared to the reference sequence. For example, the oligonucleotides disclosed herein can contain 1, 2, 3, 4, 5, or more mismatches and/or degenerate bases, as compared to the target sequence to which the oligonucleotide hybridizes, with the proviso that the oligonucleotides are capable of specifically hybridizing to the target sequence under, for example, standard nucleic acid amplification conditions.

The primers described herein can be prepared using techniques known in the art, including, but not limited to, cloning and digestion of the appropriate sequences and direct chemical synthesis. Chemical synthesis methods that can be used to make the primers of the described herein, include, but are not limited to, the phosphotriester method described by Narang et al. (1979) Methods in Enzymology 68:90, the phosphodiester method disclosed by Brown et al. (1979) Methods in Enzymology 68:109, the diethylphosphoramidate method disclosed by Beaucage et al. (1981) Tetrahedron Letters 22:1859, and the solid support method described in U.S. Pat. No. 4,458,066. The use of an automated oligonucleotide synthesizer to prepare synthetic oligonucleotide primers described herein is also contemplated herein. Additionally, if desired, the primers can be labeled using techniques known in the art and described below.

Preferably, the oligonucleotides disclosed herein are fully or substantially complementary to a target sequence or target polynucleotide, e.g., a TCS. As used herein, the terms "target polynucleotide" and "target nucleic acid" refer to a polynucleotide whose presence is to be determined in a reaction, for example an internal control sequence, and/or a sequence of sample to be measured.

Accordingly provided herein are primers that comprise, consist essentially of, or consist of a sequence of one of SEQ ID NO 3, SEQ ID NO: 4, SEQ ID NO: 5, or SEQ ID NO: 6, or a variant thereof.

Primer Sets

In some embodiments, a set of amplification primers is provided. The set of amplification primers can include one or more, e.g., 1, 2, 3, 4, 5, 6, 7, 8, 9, 10, 11, 12, 13, 14, 15, or more primer pairs. As used herein, the term "primer pair" can refer to two primers that individually hybridize to opposite strands of a target nucleic acid, e.g., a quantitative PCR internal control sequence, in which each primer can be extended at its 3' end to form a target amplification product, for example in PCR. Primer pairs can include forward and reverse primers.

In some embodiments, the compositions and methods disclosed herein include a primer pair that comprises at least one set of amplification primers that hybridize to and amplify a target control sequence. A first oligonucleotide comprising, consisting essentially of, or consisting of the sequence of SEQ ID NO: 3 and a second oligonucleotide comprising, consisting essentially of, or consisting of the sequence of SEQ ID NO: 4 is an exemplary primer pair (hereinafter "Primer Pair 5") useful in connection with the embodiments disclosed herein. A first oligonucleotide comprising consisting essentially of, or consisting of the sequence of SEQ ID NO: 5 and a second oligonucleotide comprising consisting essentially of, or consisting of the sequence of SEQ ID NO: 6 is another exemplary primer pair (hereinafter "Primer Pair 1") useful in connection with the embodiments disclosed herein. Features of Primer Pair 1 and Primer Pair 2 are described in Table 1.

TABLE 1

| Primer Name | Sequence | SEQ ID NO: | Tm (° C.) | GC % | Product Length (bp) |
|---|---|---|---|---|---|
| Primer Pair 1: Example template region: D. melanogaster genomic scaffold_CP000223.3, bp 1395700-1395900 | | | | | |
| Dros.MAX. FP1 | ATCTAGCCGTGTGCCCGCTT | 5 | 58.5 | 60.00 | 139 |
| Dros.MAX. RP1 | GGTTGTCCCATTTGTGGAGGACAGC | 6 | 59.95 | 56.00 | |

TABLE 1-continued

```
                                                            Product
Primer                                 SEQ     Tm      GC   Length
Name          Sequence                 ID NO:  (° C.)  %    (bp)

Primer Pair 5:
Example template region:
D. melanogaster genomic scaffold_CP000223.3, bp 1395700-1395900

Dros.MAX. FP5 GGATCTAGCCGTGTGCCCGCT    3       60.97   66.67  149
Dros.MAX. RP5 GGCATGGAGGTTGTCCCATTTGTG 4       58.47   54.17
```

In some embodiments, a primer pair includes a first primer that comprises the sequence of SEQ ID NO: 3 or SEQ ID NO: 5, or a variant of SEQ ID NO: 3 or SEQ ID NO:5, and a second primer that comprises a sequence of SEQ ID NO: 4 or SEQ ID NO: 6, or a variant of SEQ ID NO: 4 or SEQ ID NO: 6.

In some embodiments, a primer pair can be used to amplify an amplicon of a target control sequence (TCS), for example a template comprising the sequence of SEQ ID NO: 1, the sequence of SEQ ID NO: 8, or a variant thereof. In some embodiments, Primer Pair 1 or Primer Pair 5 is used to amplify sequences from SEQ ID NO: 1 or SEQ ID NO: 8 (e.g., template control sequences). In some embodiments, Primer Pair 5 thus produces an amplicon as shown in SEQ ID NO: 9. In some embodiments, Primer Pair 1 or Primer Pair 5 amplifies a template comprising a variant of SEQ ID NO: 1, for example, the sequence of SEQ ID NO: 10, 11, 12, or 13. In some embodiments, Primer Pair 1 or Primer Pair 5 amplifies a template comprising Drosophila genomic DNA, or a genomic fragment.

Probes

In some embodiments, sequence-specific probes are provided. Probes include, but are not limited to oligonucleotides as described herein. In some embodiments, the sequence-specific probes disclosed herein specifically hybridize to a target sequence, such as a TCS. In some embodiments, the sequence-specific probe specifically hybridizes to, and is fully or substantially complementary a nucleotide sequence flanked by the binding sites of a forward primer and reverse primer disclosed herein. In some embodiments, the sequence specific probes comprise at least 5, 6, 7, 8, 9, 10, 11, 12, 13, 14, 15, 16, 17, 18, 19, 20, 21, 22, 23, 24, or 25 nucleotides of SEQ ID NO:3, 4, 5, or 6, such that the sequence specific probe overlaps with the binding site of an amplification primer disclosed herein.

Different types of detectable moieties have been described for the detection of amplification products. One class of detectable moieties is intercalating agents, which bind non-specifically to double-stranded nucleic acid. Intercalating agents have a relatively low fluorescence when unbound, and a relatively high fluorescence upon binding to double-stranded nucleic acids. As such, intercalating agents can be used to monitor the accumulation of double strained nucleic acids during a nucleic acid amplification reaction. Examples of such non-specific dyes include intercalating agents such as SYBR Green I (Molecular Probes), propidium iodide, ethidium bromide, and the like. Other types of detectable moities employ derivatives of sequence-specific nucleic acid probes. For example, oligonucleotide probes labeled with one or more dyes, such that upon hybridization to a template nucleic acid, a detectable change in fluorescence is generated. While non-specific dyes may be desirable for some applications, sequence-specific probes can provide more accurate measurements of amplification. One configuration of sequence-specific probe can include one end of the probe tethered to a fluorophore, and the other end of the probe tethered to a quencher. When the probe is unhybridized, it can maintain a stem-loop configuration, in which the fluorophore is quenched by the quencher, thus preventing the fluorophore from fluorescing. When the probe is hybridized to a template nucleic sequence, it is linearized, distancing the fluorophore from the quencher, and thus permitting the fluorophore to fluoresce. Another configuration of sequence-specific probe can include a first probe tethered to a first fluorophore of a FRET pair, and a second probe tethered to a second fluorophore of a FRET pair. The first probe and second probe can be configured to hybridize to sequences of an amplicon that are within sufficient proximity to permit energy transfer by FRET when the first probe and second probe are hybridized to the same amplicon.

In some embodiments, the sequence specific probe comprises an oligonucleotide as disclosed herein conjugated to a fluorophore. In some embodiments, the probe is conjugated to two or more flurophores. Examples of fluorophores include: xanthene dyes, e.g., fluorescein and rhodamine dyes, such as fluorescein isothiocyanate (FITC), 2-[ethylamino)-3-(ethylimino)-2-7-dimethyl-3H-xanthen-9-yl]benzoic acid ethyl ester monohydrochloride (R6G)(emits a response radiation in the wavelength that ranges from about 500 to 560 nm), 1,1,3,3,3',3'-Hexamethylindodicarbocyanine iodide (HIDC) (emits a response radiation in the wavelength that ranged from about 600 to 660 nm), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g., umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3 (emits a response radiation in the wavelength that ranges from about 540 to 580 nm), Cy5 (emits a response radiation in the wavelength that ranges from about 640 to 680 nm), etc; BODIPY dyes and quinoline dyes. Specific fluorophores of interest include: Pyrene, Coumarin, Diethylaminocoumarin, FAM, Fluorescein Chlorotriazinyl, Fluorescein, R110, Eosin, JOE, R6G, HIDC, Tetramethylrhodamine, TAMRA, Lissamine, ROX, Napthofluorescein, Texas Red, Napthofluorescein, Cy3, and Cy5, and the like.

In some embodiments, the probe is conjugated to a quencher. A quencher can absorb electromagnetic radiation and dissipate it as heat, thus remaining dark. Example quenchers include Dabcyl, NFQ's, such as BHQ-1 or BHQ-2 (Biosearch), IOWA BLACK FQ (IDT), and IOWA BLACK RQ (IDT). In some embodiments, the quencher is selected to pair with a fluorphore so as to absorb electromagnetic radiation emitted by the fluorophore. Flourophore/quencher pairs useful in the compositions and methods disclosed herein are well-known in the art, and can be found, e.g., described in S. Marras, "Selection of Fluorophore and Quencher Pairs for Fluorescent Nucleic Acid Hybridization Probes" available at the world wide web site molecular-beacons.org/download/marras,mmb06%28335%293.pdf.

In some embodiments, a fluorophore is attached to a first end of the probe, and a quencher is attached to a second end of the probe. Attachment can include covalent bonding, and can optionally can include at least one linker molecule positioned between the probe and the fluorophore or quencher. In some embodiments, a fluorophore is attached to a 5' end of a probe, and a quencher is attached to a 3' end of a probe. In some embodiments, a fluorophore is attached to a 3' end of a probe, and a quencher is attached to a 5' end of a probe. Examples of probes that can be used in quantitative nucleic acid amplification include molecular beacons, SCORPIONS™ probes (Sigma) and TAQMAN™ probes (Life Technologies).

Some embodiments disclosed herein provide probes that specifically hybridize to a template control sequence or an amplicon of a template control sequence of SEQ ID NO: 1, or SEQ ID NO: 8, or a subsequence thereof. Accordingly, some embodiments disclosed herein provide a probe that hybridizes to an amplicon from the amplification of a template comprising SEQ ID NO: 1 or SEQ ID NO: 8 by one of Primer Pair 1 or Primer Pair 5. In some embodiments, the probe measures the amplification of a variant of SEQ ID NO: 1 or a subsequence thereof by hybridizing to an amplicon of at least one of SEQ ID NO: 8, 9, 10, 11, 12, or 13. Accordingly, in some embodiments, an oligonucleotide probe comprising, consisting essentially of, or consisting of the sequence of SEQ ID NO: 2 or 16, or a variant thereof, is provided. In some embodiments, the probe comprises a fluorophore and/or quencher as described herein. In preferred embodiments, probes can comprise SEQ ID NO: 2, with the fluorophore 6-carboxy-X-rhodamine ("ROX" or "R") attached to the 5' end of the probe, and the quencher IOWA BLACK Black-hole Quencher® 2 (IDT) ("BHQ") attached to the 3' end of the probe (e.g. 5'-(ROX)-TGA TGC CTC TTC ACA TTG CTC CAC CTT TCC T-BHQ-2-3').

In some embodiments, two or more probes are provided. In some embodiments, a first probe is provided and a second probe is provided. The first probe can be attached to a first FRET fluorophore. The second probe can be attached to a second FRET fluorophore. The first probe and the second probe can each be configured to hybridize to sequence of an amplicon to be quantified. In some embodiments, the first probe is configured to hybridize to a first subsequence of the amplicon, and the second probe is configured to hybridize to a second subsequence of the amplicon. In some embodiments, the first subsequence is positioned 5' of the second subsequence, and the number of bases between the 3' end of the first subsequence and the 5' end of the second subsequence is no more than about 10 bases, for example 10, 9, 8, 7, 6, 5, 4, 3, 2, 1, or 0 bases. In some embodiments, the first probe and the second probe each hybridize to a sequence that is a subsequence of SEQ ID NO: 1 or a variant thereof. In some embodiments, the first probe comprises the sequence of SEQ ID NO: 2, or a variant or subsequence of SEQ ID NO: 2, and the second probe is as described herein.

Vectors

In some embodiments, the nucleic acid sequences provided herein (e.g., a TCS) are present within a vector, for example a plasmid or a virus. Vectors are well-known in the art, and a person skilled in the art will appreciate that many vectors can be used to provide a nucleic acid sequence. Moreover, many variants of vectors exist, and additional vectors can be produced by a person skilled in the art. Vectors can be modified by site-directed mutagenesis, by random mutagenesis, or by one or more cloning steps to add, remove, and/or substitute at least one nucleic acid sequence of the vector, for example a multiple cloning site, an antibiotic resistance gene, an origin or replication, or a gene encoding a marker that facilitates visualization of the cells carrying the vector such as beta galactosidase, luciferase, or green fluorescent protein.

In some embodiments, the vector contains a nucleic acid amplification template sequence. The nucleic acid amplification template sequence can be moved to a different vector, for example by restriction digest to remove the nucleic acid amplification template sequence from a first vector and ligation to insert the nucleic acid amplification template sequence into a second vector, or by nucleic acid amplification, for example PCR amplification of the nucleic acid amplification template sequence, and ligation of the nucleic acid amplification template sequence into a second vector.

By way of example, a plasmid derived from pUC 119 is shown in SEQ ID NO: 7. In some embodiments, a plasmid that does not contain an internal control template sequence (e.g., a TCS), for example the plasmid of SEQ ID NO: 7 can be used as a negative control in NAT assays. The sequence of a pUC119-derived plasmid that contains the PCR template sequence of SEQ ID NO: 1 is provided in SEQ ID NO: 8. FIG. 1 illustrates a map of a plasmid comprising the sequence of SEQ ID NO: 8.

Variants

A person skilled in the art will appreciate that variants of a listed nucleic acid sequence can be generated using techniques known in the art, for example by random mutagenesis, site-directed mutagenesis, or chemical synthesis of a desired variant. In some embodiments, variants of the listed sequences are provided, in which each variant has a sequence that differs from a reference sequence by at least one nucleotide. In some embodiments, a variant nucleic acid comprises a substantially complementary sequence having at least about 70% nt-nt identity to a reference sequence, for example at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.3%, 99.5%, 99.7%, 99.8%, 99.9%, or 99.99%, including ranges between any two of the listed values.

In some embodiments, a variant has a substantially equivalent or similar function to a reference sequence. For example, for a reference sequence having primer and/or probe binding sites, many variants in nucleic acids outside of the primer and/or probe biding side do not affect primer binding and subsequent amplification, or probe hybridization.

In some embodiments, a variant of a reference template is amplified by the same primers as the reference template. In some embodiments, a variant of a reference probe hybridization site hybridizes to the same probe as the reference sequence. In some embodiments, a variant of a TCS is amplified by the same primers, and hybridized by the same primers as the TCS. In some embodiments, a variant of a TCS is provided, and one or more corresponding variant primers are provided to anneal to the variant TCS. In some embodiments, a variant of a probe binding site is provided, and one or more corresponding variant probes are provided to hybridize to the variant probe binding site. In some embodiments, a variant of a quantitative nucleic acid amplification internal control sequence is provided, and corresponding variant primers/or probes are provided to anneal to the variant internal control sequence.

In some embodiments, a variant results in a partial mismatch in a primer and/or probe hybridization site, but still permits binding of the primer or the probe. The variant can be in the probe and/or the primer. Alternatively the variant can be in the sequence to which the probe and/or primer binds. In some embodiments, a primer or probe variant results in a mismatch of no more than 5 nucleic acids, for example 5, 4, 3, 2, or 1 nucleotide. In some embodiments, even when there are mismatches, a primer can anneal to a binding site and function for PCR amplification, so long as the mismatches are not in the first two nucleotides of the 3' end of the primer. In some embodiments, even when there are mismatches, a probe can hybridize to a target sequence, regardless of the positions of the mismatches.

In some embodiments, a variant PCR primer or probe binds to the target sequence with an annealing temperature as described herein, and thus is functional for amplification and/or detection of a nucleic acid sequence.

In some embodiments, a variant having at least about 85%, e.g., at least about 86%, 87%, 88%, 89%, 90%, 91%, 92%, 93%, 94%, 95%, 96%, 97%, 98%, 99%, or more, sequence identity to SEQ ID NO: 1 is provided. SEQ ID NO: 1 represents an isolated sequence of Drosophila melanogaster. When the primers of SEQ ID NO: 3 and SEQ ID NO: 4 are used to amplify SEQ ID NO: 1, the sequence of SEQ ID NO: 9 is produced. In some embodiments, a primer pair that includes a forward primer comprising the sequence of SEQ ID NO: 3 or SEQ ID NO: 5, and a reverse primer comprising the sequence of SEQ ID NO: 4 or SEQ ID NO: 6 is used to amplify genomic DNA of Drosophila melanogaster. Because of the presence of repeats in this genomic DNA, sequences comprising SEQ ID NO: 8, 9, 10, or 11, or subsequences thereof can be produced by primer pairs described herein. In some embodiments, although a sequence comprises a 2, 3, 4, 5, 6, 7, 8, 9, 10, 15, 20, or more nucleotide variant of the sequence of SEQ ID NO: 1, this sequence can be amplified by a primer pair that includes one of a primer comprising the sequence of SEQ ID NO: 3 or SEQ ID NO: 5, and one of a primer comprising the sequence of SEQ ID NO: 4 or SEQ ID NO: 6, and/or can be hybridized by the probe of SEQ ID NO: 2.

Methods

Provided herein are methods of using the compositions disclosed herein, e.g., to monitor the efficiency of NAT assay performance. In some embodiments, the compositions disclosed herein can be used to monitor the efficiency of test sample preparation, as well as processing. For examples, in some embodiments, the compositions provided herein can be combined with test samples, and used to monitor nucleic acid extraction and/or processing (e.g., amplification and/or detection). In some embodiments, the compositions provided herein are not combined with test samples, but are processed in parallel to monitor nucleic acid extraction and/or processing (e.g., amplification and/or detection). In some embodiments, primers and nucleic acid templates disclosed herein provide a robust and reproducible method to determine the extraction efficiency, or other performance metrics of various automated or manual processes sample processing systems while additionally serving as a control for the amplification of various analytes. For example, the compositions disclosed herein can be advantageously used in connection with devices that automatically perform NAT assays, including but not limited to devices that automatically prepare and process samples in NAT assays (e.g., automatically perform nucleic acid extraction and preparation, as well as amplification and detection).

In some embodiments, extraction performance controls are provided. Nucleic acids can be extracted from various types of specimens, including biological or clinical specimens for example tissue samples, bodily fluids, or cell culture samples, as well as food samples, soil samples, or the like, using a variety of techniques known in the art. Nucleic acid extraction can include separating nucleic acids from other substances in a biological sample, for example, proteins, lipids, membranes, organelles, carbohydrates, and inorganic molecules. Nucleic acid extraction can be performed manually, or by one of a variety of automated systems. Methods provided herein can be useful to monitor efficiency of nucleic acid extraction, for example to validate an extraction method, device, and/or reagent, to provide a positive control when the extraction process is performed, and/or to perform a maintenance check on one or more component of an automated processing device.

In some embodiments, a known quantity of nucleic acid template, e.g., a target control sequence (TCS) is added to a biological sample e.g., SEQ ID NOs: 1, 8, 9, 10, 11, 12, 13, a variant thereof, or the reverse complement thereof. In some embodiments, the known quantity of nucleic acid template is added to a test ample before performing any steps of a nucleic acid extraction protocol. In some embodiments, the known quantity of nucleic acid template is added after at least one step in a nucleic acid extraction protocol has been performed.

In some embodiments, the compositions disclosed herein can be used in nucleic acid amplification methods. In some embodiments, nucleic acid amplification can include quantitative nucleic acids amplification, e.g. to measure to relative or absolute amount of nucleic acid present in a sample. In some embodiments, nucleic acid can include qualitative nucleic acid amplification, e.g. to determine whether a nucleic acid sequence is present or absent in a sample. In some embodiments, nucleic acid amplification can include quantitative and qualitative nucleic acid amplification, e.g. to determine whether a nucleic acid sequence is present in a sample, and if present, to measure the relative or absolute amount of nucleic acid sequence present in the sample. Methods of nucleic acid amplification can include, but are not limited to: polymerase chain reaction (PCR), strand displacement amplification (SDA), for example multiple displacement amplification (MDA), loop-mediated isothermal amplification (LAMP), ligase chain reaction (LCR), immuno-amplification, and a variety of transcription-based amplification procedures, including transcription-mediated amplification (TMA), nucleic acid sequence based amplification (NASBA), self-sustained sequence replication (3SR), and rolling circle amplification. See, e.g., Mullis, "Process for Amplifying, Detecting, and/or Cloning Nucleic Acid Sequences," U.S. Pat. No. 4,683,195; Walker, "Strand Displacement Amplification," U.S. Pat. No. 5,455,166; Dean et al, "Multiple displacement amplification," U.S. Pat. No. 6,977,148; Notomi et al., "Process for Synthesizing Nucleic Acid," U.S. Pat. No. 6,410,278; Landegren et al. U.S. Pat. No. 4,988,617 "Method of detecting a nucleotide change in nucleic acids"; Birkenmeyer, "Amplification of Target Nucleic Acids Using Gap Filling Ligase Chain Reaction," U.S. Pat. No. 5,427,930; Cashman, "Blocked-Polymerase Polynucleotide Immunoassay Method and Kit," U.S. Pat. No. 5,849,478; Kacian et al., "Nucleic Acid Sequence Amplification Methods," U.S. Pat. No. 5,399,491; Malek et al., "Enhanced Nucleic Acid Amplification Process," U.S. Pat. No. 5,130,238; Lizardi et al., BioTechnology, 6:1197 (1988); Lizardi et al., U.S. Pat. No. 5,854,033 "Rolling circle replication reporter systems." In some embodiments, two or more of the listed nucleic acid amplification methods are performed, for example sequentially.

In some embodiments, a series of individual amplification reactions are performed with known quantities of nucleic acid temples, such as template control sequences (TCSs) as disclosed herein, to generate a standard curve. Based upon the standard curve, the quantity of target template in separate amplification reactions can be determined. In some embodiments, a known quantity of internal control template (e.g., a template control sequence such as SEQ ID NO: 1, 8, 9, 10, 11, 12 or 13, or a variant thereof) is combined with a sample that may or may not contain a target nucleic acid to be amplified, and both the template control sequence and the target nucleic acid (if present) are amplified in a multiplex reaction. In some embodiments, a series of nucleic acid amplification reactions, each reaction having a known quantity of the template control sequence (e.g., SEQ ID NO:1, 8, 9, 10, 11, 12, or 13), and a detection threshold is determined for each quantity of internal control template, thereby generating a standard curve. In some embodiments, multiple replicates of each quantity of control template are performed, for example 2, 3, 4, 5, 6, 7, 8, 9, or 10 replicates. The standard curve for the internal control sequence can then be used to determine the amount of target reaction in a sample. Multiplex and standard-curve method of nucleic acid quantification are described in detail by McMillan et al (U.S. Pat. No. 6,783,934). In some embodiments, the number of amplification cycles performed until a target amplicon reaches a detection threshold is calculated ("Cq"). In some embodiments, the method includes providing a probe in the amplification reaction. For example, in some embodiments, a non sequence-specific probe is provided. In some embodiments, the methods disclosed herein include providing a sequence-specific probe in the amplification reaction, e.g., a probe comprising, consisting of, or consisting essentially of, SEQ ID NO: 2, or a variant thereof.

In some embodiments, the method includes detecting the amount of amplicon produced. The detection can be performed continuously or periodically. For example detection can be performed at the end of every Nth cycle or fraction therof, where N is one of 1, 2, 3, 4, 5, 6, 7, 8, 9, 10, 11, 12, 13, 14, 15, 16, 17, 18, 19, 20, or the like. In some embodiments, detection can include measuring fluorescence, for example the intensity of electromagnetic radiation at the emission wavelength of the flurophore tethered to the probe, or a wavelength range including the emission wavelength of the flurophore tethered to the probe. In some embodiments, detection can include detecting FRET.

In some embodiments, the efficiency of quantitative nucleic amplification is measured. It can be useful to measure the efficiency of a quantitative nucleic amplification reaction, for example to determine the sensitivity of the reaction to low-copy-number nucleic acids, or to optimize or validate a protocol, reagent, and/or device for quantitative nucleic acid amplification. In some embodiments, a known quantity of nucleic acid template is added to a quantitative nucleic acid reaction. In some embodiments, the template is an internal control template. In some embodiments a primer pair configured to amplify an amplicon of the nucleic acid template is added to the reaction. The forward primer and reverse primer of the primer pair can hybridize to the template and be extended, thus producing an amplicon. The amount of amplicon produced can be monitored at one or more timepoints during the amplification reaction, or can be monitored continuously using methods disclosed herein. In some embodiments, a threshold cycle Cq can be defined as a level of relative fluorescence units (RFU's), for example about 100, 200, 300, 400, 500, 600, 700, 800, 900, 1000, 1100, 1200, 1300, 1400, 1500, 1700, 2000, 2500, or 3000 RFU's. In Example 2 herein, Cq is defined as 500 RFU's. In some embodiments, the standard curve is represented as Cq versus the starting quantity of template, or a logarithmic transformation thereof. In some embodiments, the standard curve is represented as relative fluorescent units versus the starting quantity of template, or a logarithmic transformation thereof.

In some embodiments, the known quantity of nucleic acid template is quantified by a quantitative nucleic acid amplification reaction as described herein, for example quantitative PCR. In some embodiments, for example in embodiment in which an RNA is being extracted, RNA is reverse transcribed into DNA prior to the quantification step. In some embodiments, the known quantity of nucleic acid template is quantified after the extraction procedure has been completed. In some embodiments, the known quantity of nucleic acid template is quantified after an intermediate step in the extraction process, for example to determine the efficiency of a subsequent step of the extraction process.

The skilled artisan will appreciate that the compositions disclosed herein can be used in various types of nucleic acid amplification reactions, as disclosed herein. In some embodiments, the compositions disclosed herein can be used in polymerase chain reaction (PCR). For a review of PCR technology, including standard PCR conditions, applied to clinical microbiology, see DNA Methods in Clinical Microbiology, Singleton P., published by Dordrecht; Boston: Kluwer Academic, (2000) Molecular Cloning to Genetic Engineering White, B. A. Ed. in *Methods in Molecular Biology* 67: Humana Press, Totowa (1997) and "PCR Methods and Applications", from 1991 to 1995 (Cold Spring Harbor Laboratory Press). Non-limiting examples of "PCR conditions" include the conditions disclosed in the references cited herein, such as, for example, 50 mM KCl, 10 mM Tris-HCl (pH 9.0), 0.1% Triton X-100, 2.5 mM $MgCl_2$, with an annealing temperature of 72° C.; or 4 mM $MgCl_2$, 100 mM Tris, pH 8.3, 10 mM KCl, 5 mM $(NH_4)_2SO_4$, 0.15 mg BSA, 4% Trehalose, with an annealing temperature of 59° C., or 50 mM KCl, 10 mM Tris-HCl (pH 9.0), 0.1% Triton X-100, 2.5 mM $MgCl_2$, with an annealing temperature of 55° C., or the like.

In some embodiments, at least one polymerase is provided. The polymerase can be used for quantitative PCR. Different nucleic acid polymerases are available for use, including but not limited to the FASTSTART™ Taq DNA polymerase (Roche), the KlenTaq 1 (AB peptides Inc.), the HOTGOLDSTAR™ DNA polymerase (Eurogentec), the KAPATAQ™ HotStart DNA polymerase or the KAPA2G™ Fast HotStart DNA polymerase (Kapa Biosystemss), and the PHUSION™ Hot Start (Finnzymes).

In some embodiments, a single primer, e.g., SEQ ID NO: 3, 4, 5, 6, or variants thereof is used for amplification Thermal Cycling Thermal cycling conditions can vary in time as well as in temperature for each of the different steps, depending on the thermal cycler used as well as other variables that could modify the amplification's performance. In some embodiments, a 2-step protocol is performed, in which the protocol combines the annealing and elongation steps at a common temperature, optimal for both the annealing of the primers and probes as well as for the extension step. In some embodiments, a 3-step protocol is performed, in which a denaturation step, an annealing step, and an elongation step are performed.

In some embodiments, the compositions disclosed herein can be used in connection with devices for real-time amplification reactions, e.g., the BD MAX® (Becton Dickinson and Co., Franklin Lakes, N.J.), the VIPER® (Becton Dickinson and Co., Franklin Lakes, N.J.), the VIPER LT® (Becton Dickinson and Co., Franklin Lakes, N.J.), the SMARTCYLCER® (Cepheid, Sunnyvale, Calif.), ABI PRISM 7700® (Applied Biosystems, Foster City, Calif.), ROTOR-GENE™ (Corbett Research, Sydney, Australia), LIGHTCYCLER® (Roche Diagnostics Corp, Indianapolis, Ind.), ICYCLER® (BioRad Laboratories, Hercules, Calif.), IMX4000® (Stratagene, La Jolla, Calif.), CFX96™ Real-Time PCR System (Bio-Rad Laboratories Inc), and the like.

Isothermal Amplification

In some embodiments, the compositions disclosed herein can be used in methods comprising isothermal amplification of nucleic acids. Isothermal amplification conditions can vary in time as well as temperature, depending on variables such as the method, enzyme, template, and primer or primers used. Examples of amplification methods that can be performed under isothermal conditions include, but are not limited to, some versions of LAMP, SDA, and the like.

Isothermal amplification can include an optional denaturation step, followed by an isothermal incubation in which nucleic acid is amplified. In some embodiments, an isothermal incubation is performed without an initial denaturing step. In some embodiments, the isothermal incubation is performed at least about 25° C., for example about 25° C., 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75° C., including ranges between any of the listed values. In some embodiments, the isothermal incubation is performed at about 37° C. In some embodiments, the isothermal incubation is performed at about 64° C. In some embodiments, the isothermal incubation is performed for 180 minutes or less, for example about 180, 165, 150, 135, 120, 105, 90, 75, 60, 45, 30, or 15 minutes, including ranges between any two of the listed values.

In Situ Hybridization

In some embodiments, methods of in situ hybridization are provided. In situ hybridization can be performed on samples as described herein, or sections thereof. In some embodiments, in situ hybridization can be used to identify localization of a nucleic acid target sequence, for example intracellularly, among a population of cells, within a tissue or organ, and/or within a whole organism. In some embodiments, in situ hybridization is used to quantify the number of copies of a target nucleic acid in a sample. In some embodiments, a probe as described herein can be used in in situ hybridization. In some embodiments, the probe can include an oligonucleotide consisting substantially of SEQ ID NO: 2, or a variant and/or a subsequence thereof. In some embodiments, the probe can include an oligonucleotide comprising or consisting substantially of one of SEQ ID NO: 3-6, or a variant and/or a subsequence thereof.

Master Mix

In some embodiments, a master mix is provided. A master mix can include at least two reagents for an assay that are provided in relative concentrations that are proportional to the relative concentrations of the reagents in a NAT assay Thus, a single a single quantity of master mix can be added to a reaction to provide appropriate relative concentrations of two or more reagents. In some embodiments, a master mix can include at least two of: polymerase, buffer, salts, for example magnesium, nucleotide triphosphates, a primer pair, and water. In some embodiments, a master mix can be provided at a higher concentration than will be used in a reaction. In some embodiments, a master mix is provided in a lyophilized form, and reconstituted at a higher concentration that will be used in the reaction. In some embodiments a master mix includes reagents at a concentration of at least about 2× of the reaction concentration, for example 2×, 2.5×, 3×, 4×, 5×, 6×, 7×, 8×, 9×, 10×, 15×, 20×, 25×, 40×, 50×, 100×, 200×, 250×, or 500×.

Kits

In some embodiments kits are provided. In some embodiments, a kit includes one or more of: a primer pair, a one probe. a template polynucleotide, for example a quantitative NAT internal control template sequence, a polymerase, a buffer, one or more nucleotides (e.g., a dNTP mix), instructions, or packaging. In some embodiments, at least one reagent of the kit is provided in a master mix.

In some embodiments, an internal control template, at least one primer pair for amplifying the internal control template, and at least one probe that hybridized to an amplicon of the primer pair is provided along with at least one primer pair and at least one probe for a target polynucleotide.

In some embodiments, the internal control sequence of the kit includes a polynucleotide template comprising at least one of SEQ ID NO: 1, SEQ ID NO: 8, SEQ ID NO: 9, SEQ ID NO: 10, SEQ ID NO: 11, SEQ ID NO: 12, or SEQ ID NO: 13.

In some embodiments, the kit includes at least one primer as described herein, for example an oligonucleotide comprising one of SEQ ID NO: 3, SEQ ID NO: 4, SEQ ID NO: 5, or SEQ ID NO: 6. In some embodiments, the kit includes at least one primer pair as described herein, for example Primer Pair 1, and/or Primer Pair 5.

In some embodiments, the kit includes at least one probe as described herein, for example an oligonucleotide probe comprising SEQ ID NO: 2 or 16.

In some embodiments, the kit includes at least one of: reverse transcriptase; RNAse, for example RNAase H; or RNA polymerase, for example T7 RNA polymerase, or the like.

EXAMPLE 1

Quantitaive PCR with Sensitivity, Robustness, and Reproducibility

In order to assess the sensitivity, robustness, and reproducibility of the compositions disclosed herein as control/standard sequences, a series of polymerase chain reaction amplification reactions was performed.

Each reaction included a known number of copies of a template plasmid, a TAQMAN™ (Life Technologies) probe having the sequence of SEQ ID NO: 2 (or SEQ ID NO: 16 in the case of assays shown in FIG. 4D), and one of Primer Pair 1 or Primer Pair 5. In the assays depicted in FIGS. 3A, 3B, 4A, 4B, 4C, and 4D, the template was a plasmid having the sequence of SEQ ID NO: 8. In the assays depicted in FIG. 5, the template was a linearized plasmid having the sequence of SEQ ID NO: 15. Reactions were performed with 5 copies of template, 50 copies of template, and 500 copies of template, and four replicates were performed. Real-time PCR was performed in optical 96-well reaction plates using the CFX96™ Real-Time PCR System (Bio-Rad Laboratories Inc,). The thermal cycling profile was: 95° C., 15 min (1 cycle); 95° C., 15 sec, 60° C., 1 min (50 cycles). The PCR reactions conditions were: Tris pH 8.0 (70 mM), NaOH 5.0 mM, Reverse Primer 0.60 uM, Forward Primer 0.60 uM, Dros.MAX probes (0.40 uM) (Note: there were 4 different probe lots used, as described herein), $MgCl_2$ (3.5 mM), dATP (0.05 mM), dCTP (0.05 mM), dGTP (0.05 mM), dTTP (0.05 mM), HGS polymerase (2.7 Units). For each quantity of template, the amount of product at the end of each cycle was measured in Relative Fluorescent Units, and the number of cycles (Cq) needed to detect a threshold level of product (as measured by hybridization of fluorescent probe) was determined. The threshold level of Cq was set at 500 RFU's.

Figure 3A:
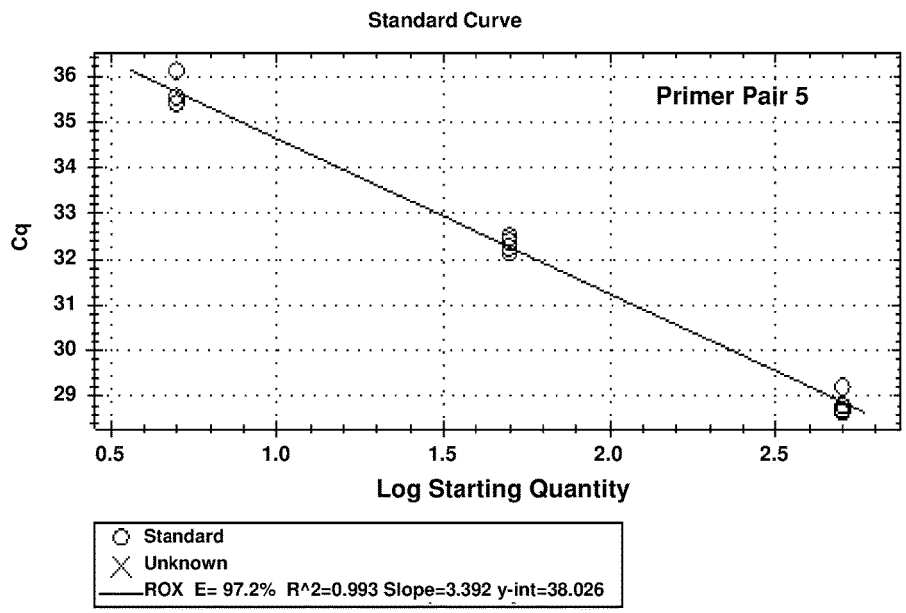
FIG. 3A illustrates a standard curve derived from real-time amplification reactions of 5 copies of template, 50 copies of template, and 500 copies of internal control template comprising SEQ ID NO: 8 using amplification Primer Pair 5. For each starting quantity of 5 copies of template, 50 copies of template, and 500 copies of template, four replicates were performed, and Cq was determined. The standard curve represents Cq versus the log starting quantity of template.
Figure 3B:
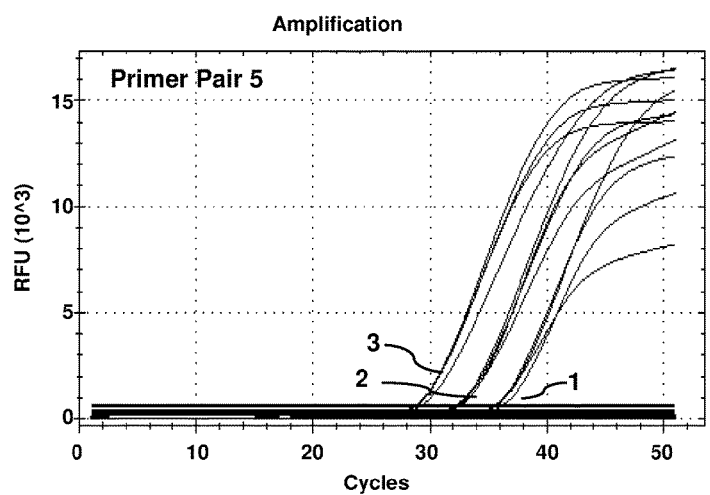
FIG. 3B shows amplification curves (fluorescence versus cycle) for the series of amplification reactions used to generate the standard curve shown in FIG. 3A.

FIGS. 3A, 3B, 4A, 4B, 4C, and 4D illustrate results of these assays. Highly reproducible results were obtained, even for reactions having only 5 copies of plasmid. As shown in FIG. 3A, a standard curve plotting the copy number of template against the Cq for each of the replicates had an $R^2$ value of 0.993.

The amplification curves shown in FIGS. 4A, 4C, and 4D demonstrate high sensitivity and reproducibility for Primer Pair 5, and FIG. 4B demonstrates high sensitivity and reproducibility for Primer Pair 1 for quantitative PCR reactions at 200, 50, 25, and 5 copies of plasmid per PCR reaction. FIGS. 4A, 4B, and 4C represent results in which each assay used probe from a different probe lot (FIG. 4A=lot 1; FIG. 4B=lot 2, FIG. 4C=lot 3) and having the sequence of SEQ ID NO: 2 (i.e. a single "T" on the 5' end of the probe), while FIG. 4D represents results from assay using probes having the sequence of SEQ ID NO: 16 (i.e. a "TT" doublet on the 5' end of the probe). The results of FIG. 4D demonstrate that the system has high sensitivity and reproducibility, even when variant probes are used (note that the probe of SEQ ID NO: 16 does not fully complement the probe binding sequence of the template of SEQ ID NO: 8, as the T on the 5' end of the probe corresponds to a "C" on the equivalent strand of SEQ ID NO: 16). As shown in FIG. 4B, the detection threshold and amplification rate was reproducible and sensitive for reactions having 5 copies of template (reference numeral 1), 50 copies of template (reference numeral 2), and 500 copies of template (reference numeral 3).

EXAMPLE 2

Quantitative Amplification Reaction

Cell samples are collected. RNA is isolated from the cell samples. The isolated sample RNAs are reverse-transcribed, thus producing sample cDNAs. A lyophilized master mix that includes polymerase, buffer, magnesium, and nucleotide triphosphates is reconstituted to 2× concentration by adding diluent. Equal parts of master mix and a liquid that includes: a 2× concentration of sample cDNAs (or a negative control or positive control); primers for amplifying a viral RNA marker, SCORPION™ probe for measuring amount of amplified viral marker, and internal control nucleic acids are combined in thin-walled plastic assay tubes.

An internal control is present in each assay test tube to monitor PCR reagent integrity and detect the presence of PCR inhibitors. Two external controls are also performed: one negative control containing all the reagents but no template DNA; and one positive control which is a sample known to contain the targeted gene, are processed as samples, but are run to serve as controls. All controls are performed at the same time, using the same reagents, in the same amplification reaction. The internal control is performed using a template that includes a plasmid having the nucleic acid sequence of SEQ ID NO: 8. The internal control includes a primer pair that includes a first oligonucleotide primer having the sequence of SEQ ID NO: 3, and a second oligonucleotide primer having the sequence of SEQ ID NO: 4. The primer pair will amplify a subsequence of SEQ ID NO: 6, producing a polynucleotide product having the sequence of SEQ ID NO: 7. The internal control includes a SCORPION™ probe of the sequence of SEQ ID NO: 2.

The reaction mixture is a classic combination of template nucleic acid, oligonucleotide primers at a concentration around 0.4 µM of each, probe at around 0.35 µM, proper buffer for the enzyme, salts (MgCl2 in this case), and of course the polymerase enzyme in a minimum concentration around 0.06 U/rx. The FastStart Taq DNA polymerase enzyme is used as polymerase. Also added to the reaction mixture are deoxyribonucleotide triphosphates (dNTPs) in a concentration around 0.15 mM for each (dTTP, dATP, dGTP and dCTP), as well as bovine serum albumin (BSA) at around 0.15 mg/mL. BSA is optional, and can help the reaction to perform even in the presence of PCR inhibitors.

Cycling conditions that will allow the primer extension and amplification of the target DNA include a denaturation step, an annealing step and a polymerization step. The first step is a 15 minutes initial denaturation step at 95° C. It is followed by a short denaturation step at 95° C. for 1 second, the annealing step at 60° C. for 9 seconds and an elongation step at 72° C. for 10 seconds. This cycle is repeated 45 times. There is also a final elongation step of 10 minutes at 72° C. at the end, to ensure that the enzyme finishes extending every single-stranded DNA.

After each cycle of amplification, the amount of internal control polynucleotide product is measured by the intensity of fluorescence intensity (in Relative Fluorescence Unites) emitted by the fluorophore of the internal control SCORPION™ probe.

What is claimed is:

1. A composition comprising:
   a polynucleotide comprising a sequence at least 97% identical to the sequence of SEQ ID NO: 1;
   a forward primer comprising an oligonucleotide at least 85% identical to SEQ ID NO: 3 or 5;
   a reverse primer comprising an oligonucleotide at least 85% identical to SEQ ID NO: 4 or 6;
   a single-stranded oligonucleotide probe comprising a detectable moiety attached thereto and a sequence at least 85% identical to SEQ ID NO: 2; and
   a sample, wherein the sample does not comprise genomic DNA of the genus *Drosophila*.

2. The composition of claim 1, wherein the forward primer is at least 95% identical to SEQ ID NO: 3.

3. The composition of claim 1, wherein the reverse primer is at least 95% identical to SEQ ID NO: 4.

4. The composition of claim 1, wherein the forward primer comprises SEQ ID NO: 3, and the reverse primer comprises SEQ ID NO: 4.

5. The composition of claim 1, wherein the forward primer comprises SEQ ID NO: 5, and the reverse primer comprises SEQ ID NO: 6.

6. The composition of claim 1, wherein the single-stranded oligonucleotide probe comprises a sequence at least 95% identical to SEQ ID NO: 2.

7. The composition of claim 1, wherein the single-stranded oligonucleotide probe comprises SEQ ID NO: 2.

8. The composition of claim 1, wherein the single-stranded oligonucleotide probe further comprises at least one fluorophore, and at least one quencher.

9. The composition of claim 1, wherein the forward primer is at least 95% identical to SEQ ID NO: 5.

10. The composition of claim 1, wherein the reverse primer is at least 95% identical to SEQ ID NO: 6.

11. The composition of claim 1, wherein the sequence of the polynucleotide is not genomic DNA sequence of an organism of the genus *Drosophila*.

12. A kit comprising:
   an isolated nucleic acid template for nucleic acid amplification comprising a sequence having at least 97% identity to SEQ ID NO 1;
   a first primer comprising an oligonucleotide having at least 85% identity to SEQ ID NO: 3 or 5;
   a second primer comprising an oligonucleotide having at least 85% identity to SEQ ID NO: 4 or: 6; and an oligonucleotide probe comprising a detectable moiety attached thereto and an oligonucleotide comprising a sequence at least 85% identical to SEQ ID NO: 2.

13. The kit of claim 12, wherein the first primer comprises an oligonucleotide having at least 95% identity to SEQ ID NO: 3 or 5.

14. The kit of claim 12, wherein the second primer comprises an oligonucleotide having at least 95% identity to SEQ ID NO: 4 or 6.

15. The kit of claim 12, wherein the first primer comprises SEQ ID NO: 3 or 5.

16. The kit of claim 12, wherein the second primer comprises SEQ ID NO: 4 or 6.

17. The kit of claim 12, wherein the first primer comprises SEQ ID NO: 3 and the second primer comprises SEQ ID NO: 4, or wherein the first primer comprises SEQ ID NO: 5 and the second primer SEQ ID NO: 6.

18. The kit of claim 17, wherein the oligonucleotide probe comprises SEQ ID NO: 2.

19. The kit of claim 12, wherein the oligonucleotide probe comprises SEQ ID NO: 2.

20. An isolated nucleic acid that comprises SEQ ID NO: 1.

* * * * *